(12) United States Patent
Barthelemy et al.

(10) Patent No.: US 10,633,409 B2
(45) Date of Patent: Apr. 28, 2020

(54) BOLA-AMPHIPHILIC COMPOUNDS AND THEIR USES FOR BIOMEDICAL APPLICATIONS

(71) Applicants: UNIVERSITE DE BORDEAUX, Bordeaux (FR); INSTITUT NATIONAL DE LA SANTE ET DE LA RECHERCHE MEDICALE (INSERM), Paris (FR)

(72) Inventors: Philippe Barthelemy, Merignac (FR); Michael Ramin, Bordeaux (FR); Laurent Latxague, Saint-Medard-en-Jalles (FR); Ananda Appavoo, Bordeaux (FR); Olivier Chassande, Pessac (FR); Camille Ehret, Haguenau (FR)

(73) Assignees: UNIVERSITE DE BORDEAUX, Bordeaux (FR); INSTITUT NATIONAL DE LA SANTE ET DE LA RECHERCHE MEDICALE (INSERM), Paris (FR)

(*) Notice: Subject to any disclaimer, the term of this patent is extended or adjusted under 35 U.S.C. 154(b) by 0 days.

(21) Appl. No.: 16/251,287

(22) Filed: Jan. 18, 2019

(65) Prior Publication Data

US 2019/0233460 A1    Aug. 1, 2019

Related U.S. Application Data

(62) Division of application No. 15/517,313, filed as application No. PCT/EP2015/073072 on Oct. 6, 2015, now Pat. No. 10,227,372.

(30) Foreign Application Priority Data

Oct. 6, 2014 (EP) .................................. 14290302

(51) Int. Cl.
| | |
|---|---|
| *C07H 19/06* | (2006.01) |
| *C07H 1/00* | (2006.01) |
| *C07H 19/073* | (2006.01) |
| *A61K 9/06* | (2006.01) |
| *A61K 47/26* | (2006.01) |
| *C12N 5/00* | (2006.01) |

(52) U.S. Cl.
CPC .............. *C07H 19/06* (2013.01); *A61K 9/06* (2013.01); *A61K 47/26* (2013.01); *C07H 1/00* (2013.01); *C07H 19/073* (2013.01); *C12N 5/0068* (2013.01); *C12N 2513/00* (2013.01); *C12N 2533/20* (2013.01); *C12N 2539/00* (2013.01)

(58) Field of Classification Search
CPC ........ A61K 8/69; A61Q 19/02; C07C 43/253; C07C 2601/14; C07C 43/247
See application file for complete search history.

(56) References Cited

FOREIGN PATENT DOCUMENTS

WO    20080103618 A1    8/2008

OTHER PUBLICATIONS

Godeau, G. et al. "Glycosyl-nucleoside-lipid based supramolecular assembly as a nanostructured material with nucleic acid delivery capabilities" Chem. Commun., 2009, 5127-5129 (Year: 2009).*
Sartori, G. et al. "Protection (and Deprotection) of Functional Groups in Organic Synthesis by Heterogeneous Catalysis" Chem. Rev. 2004, 104, 199-250 (Year: 2004).*
Guilhem Godea et al.,"Glycosyl-nucleoside-lipid based supramolecular assembly as a nanostructured material with nucleic acid delivery capabilities", Chemical Communication, p. 5127-5129, No. 34 (Jan. 2009).
Sophia Ziane et al.,"A thermosensitive low molecular weight hydrogel as scaffold for tissue engineering", European cells & materials, pp. 147-160 (Jan. 2012).
Laurent Latxague et al.,"Glycosyl-Nucleolipids as New Bioinspired Amphiphiles", Molecules, pp. 12241-12263, vol. 18, No. 10 (Jan. 2013).
Laurent Latxague et al.,"Glycosylated nucleoside lipid promotes the liposome internalization in stem cells", Chemical Communications, pp. 12598-12600, vol. 47, No. 47 (Jan. 2011).
Nuraje Nurxat et al.,"Bolaamphiphilic molecules: Assembly and application" Progress in Polymer Science, pp. 302-343, vol. 38. No. 2 (Sep. 2012).
Godeau, G. et al. "Giycosyl-nucleoside-lipid based supramolecular assembly as a nanostructured material with nucleic acid delivery capabilities" Chem. Commun., 2009, 5127-5129 (Year: 2009).
Barthelemy, P. et al. "Giycosyi-Nucleoside Lipids as Low-Molecular-Weight Gelators" Langmuir 2009, 25(15), 8447-8450 (Year: 2009).
Iwaura, R. et al. "Oiigonucleotide-Templated Self-Assembly of Nucleotide Bolaamphiphiles: DNA-Like Nanofibers Edged by a Double-Helical Arrangement of A-T Base Pairs" Angew. Chem. Int. Ed. 2003, 42, No. 9 (Year: 2003).
Latxague, L. et al. "Giycosyi-Nucleolipids as New Bioinspired Amphiphiles" Molecules 2013, 18, 12241-12263 (Year: 2013).

(Continued)

*Primary Examiner* — Andrew S Rosenthal
(74) *Attorney, Agent, or Firm* — Browdy and Neimark, PLLC

(57) ABSTRACT

The invention relates to bola-amphiphilic compounds and their uses for biomedical application.
The invention particularly relates to the use of bola-amphiphilic compounds for providing low molecular weight gels (LMWG), useful, in particular, as culture media for animal or human cells, or as biocompatible material for biomedical applications.

2 Claims, 7 Drawing Sheets

(56) References Cited

OTHER PUBLICATIONS

Tiwari, P. et al. "Efficient Acetylation of Carbohydrates Promoted by Imidazole" Eur. J. Org. Chem. 2005, 4265-4270 (Year: 2005).
Click Chemistry—Section 3.1 from The Molecular Probes Handbook, as downloaded Oct. 25, 2019, from https://www.thermofisher.com/fr/fr/home/references/molecular-probes-the-handbook/reagents-for-modifying-groups-other-than-thiols-or-amines/click-chemistry.html.

* cited by examiner (a) Propargyl bromide, DMF, K₂CO₃, rt, 2d (86%)

(b) 2,3,4,6-tetra-O-acetyl-6-deoxy-β-D-glucopyranosyl azide, tert-butanol/H₂O (1:1), CuSO₄/sodium ascorbate, 60°C, 20h (82%)

(c) PPh₃, NaN₃, CBr₄, DMF, rt, 24H (88%)

(d) 1,1'-(dodecane-1,12-diyl)bis(3-(propargyl)urea), tert-butanol/H₂O (1:1), CuSO₄/sodium ascorbate, 60°C, 20h (78%)

(e) Propargyl amine, DCM, rt, 16h (99%)

(a) Propargyl bromide, DMF, K₂CO₃, rt, 2h (86%)
(b) 2,3,4,6-tetra-O-acetyl-6-deoxy-β-D-glucopyranosyl azide, tert-butanol/H₂O (1:1), CuSO₄/sodium ascorbate, 60°C, 20h (82%)
(c) PPh₃, NaN₃, CBr₄, DMF, rt, 24h (88%)
(d) Compound 18, tert-butanol/H₂O (1:1), CuSO₄/sodium ascorbate, 75°C, 24h (76%)
(e) Propargyl amine, DCM, rt, 16h (99%)
(f) Methoxide/methanol, 45°C, 30min (84%)

BOLA-AMPHIPHILIC COMPOUNDS AND THEIR USES FOR BIOMEDICAL APPLICATIONS

The invention relates to bola-amphiphilic compounds and their uses for biomedical applications.

The invention particularly relates to the use of bola-amphiphilic compounds for providing low molecular weight gels (LMWG), useful, in particular, as culture media for cells, in particular isolated stem cells.

Hydrogels which are non-toxic, easy to use, cytocompatible, injectable and degradable are valuable biomaterials as cell-culture media.

The development of biocompatible artificial matrixes that can be used for stem cell culture remains a great challenge in cell culture engineering and/or regenerative medicine. Most of gel scaffold developed so far involve polymeric materials derived from either natural sources or chemical synthesis. However, polymers often suffer from several limitations, including poor biocompatibility, toxicity, biodegradability, pro-inflammatory activity etc. Alternatively, small-molecule based hydrogels are currently emerging as a new powerful tool for regenerative medicine strategy capable of restoring biological and mechanical properties and/or function.

The invention thus relates to new bola-amphiphilic compounds derived from nucleolipids and to a new generation of low molecular weight gels (LMWG) which are suitable for cell culture, in particular for stem cell culture. Bola-amphiphile based hydrogel matrixes exhibit the following requested properties: non-toxicity, easy to handle, injectability, and biocompatible rheology (thixotropic behavior).

Bola-amphiphiles are composed of one or two hydrophobic chains covalently linked at both ends to hydrophilic head groups. This type of molecular architecture, which can be found in archaebacteria membranes, have been used in numerous applications which range from nanomaterial synthesis to drug or gene delivery.

The use of glycosyl-nucleosides-lipids (GNL) and glycosyl-nucleosides-fluorolipids (GNF) for forming LMWG has been reported.

GNL have been reported as being useful for promoting internalization of GNL based liposomes into stem cells (L. Latxague et al., Chem. Commun., 2011, 47, 12598-12600).

GNL supramolecular assemblies for nucleic acid delivery and GNL-based gels were studied in G. Godeau et al., Chem. Commun., 2009, 1-3.

GNF-based gels were reported as being only compatible with stem cell cultures where the stem cells formed aggregates, and clearly not compatible with the survival and growth of isolated stem cells (S. Ziane et al., Eur. Cells and Math., 2012, 23, 147-160).

It has now been found that new glycosylated nucleoside based bola-amphiphile (GNBA) compounds exhibit particular physicochemical properties which render them particularly suitable for providing low molecular weight gels.

The invention thus relates to a compound of formula (I)

(I)

in which
X is oxygen, —NH—C(O)—NH— or —C(O)—NH—
A is a $C_4$-$C_{30}$ hydrocarbon chain, linear or branched, saturated or unsaturated, which is unsubstituted or substituted by one or more $C_1$-$C_{12}$ linear or branched alkyl groups, or A represents a $C_4$-$C_{30}$ hydrocarbon chain, linear or branched, saturated or unsaturated, which is partially or completely halogenated;

$R_1$ and $R_2$, identical or different, represent hydrogen or —$(CH_2)_n$—$R_3$—$(CH_2)_m$—$R_4$—$(CH_2)_p$—$R_5$-$R_6$ in which
n, m and p, identical or different, are 0 to 10;
$R_3$ represents a heteroaryl group comprising 1 to 4 oxygen or nitrogen atom(s);
$R_4$ represents a nucleosidyl group or does not exist;
$R_5$ represents a heteroaryl group comprising 1 to 4 heteroatom(s);
$R_6$ represents a residue of a cyclic carbohydrate or a derivative of the said carbohydrate;
provided that $R_1$ and $R_2$ are not simultaneously hydrogen.

Preferably, A is a $C_4$-$C_{18}$ hydrocarbon chain, more preferably a $C_{12}$ or $C_{14}$ hydrocarbon chain, linear or branched, saturated or unsaturated, which is unsubstituted or substituted by one or more $C_1$-$C_{12}$ linear or branched alkyl groups;

Alternatively, A is a $C_4$-$C_{18}$ hydrocarbon chain, more preferably a $C_{10}$ or $C_{12}$ hydrocarbon chain linear or branched, saturated or unsaturated, which is partially or completely halogenated.

Preferably, the invention relates to compound of formula (I) in which $R_4$ represents a nucleosidyl group.

Preferably, $R_1$ and $R_2$, identical or different, represent —$(CH_2)_n$—$R_3$—$(CH_2)_m$—$R_4$—$(CH_2)_p$—$R_6$-$R_6$.

According to a preferred embodiment, the invention relates to a compound of formula (I)

(I)

in which
X is oxygen, —NH—C(O)—NH— or —C(O)—NH—
A is a $C_4$-$C_{30}$ hydrocarbon chain, linear or branched, saturated or unsaturated, which is unsubstituted or substituted by one or more $C_1$-$C_{12}$ linear or branched alkyl groups, or A represents a $C_4$-$C_{30}$ hydrocarbon chain, linear or branched, saturated or unsaturated, which is partially or completely halogenated;

$R_1$ and $R_2$, identical or different, represent —$(CH_2)_n$—$R_3$—$(CH_2)_m$—$R_4$—$(CH_2)_p$—$R_5$-$R_6$ in which
n, m and p, identical or different, are 0 to 10;
$R_3$ represents a heteroaryl group comprising 1 to 4 oxygen or nitrogen atom(s);
$R_4$ represents a nucleosidyl group;
$R_5$ represents a heteroaryl group comprising 1 to 4 heteroatom(s);
$R_6$ represents a residue of a cyclic carbohydrate or a derivative of the said carbohydrate.

$R_5$ can be covalently linked to $R_4$ via —$(CH_2)_p$— to the carbon atom at position 5' of the ribose or deoxyribose ring of the nucleoside, or, alternatively, to the oxygen atom at position 3' of the ribose or deoxyribose ring of the nucleoside.

«Heteroaryl group containing 1 to 4 oxygen or nitrogen atoms» refers to a monocyclic or bicyclic, aromatic or partially unsaturated, carbocyclic group containing 5 to 12 atoms, interrupted by 1 to 4 oxygen or nitrogen atoms, which can be, for example, selected from furane, pyrrole, oxazole, oxadiazole, isoxazole, pyrazole, triazole, tetrazole, imidazole, pyridine, pyrimidine, pyridazine, pyrazine, benzofurane, indole, quinoleine, isoquinoleine, chromane, naphtyridine or benzodiazine groups, triazole being preferred.

«Hydrocarbon chain, which is partially or completely halogenated» refers to a saturated or unsaturated alkyl chain in which some or all hydrogen atoms are replaced by halogen atoms, such as fluorine, iodine, chlorine or bromine, fluorine being preferred.

«Nucleosidyl group» refers to a group consisting of a ribose or deoxyribose moiety which is linked to a purine or pyrimidine base, or to derivatives of said purine or pyrimidine base, or to a non-natural mono- or bicyclic heterocyclic base, all said bases being optionally substituted.

The purine base can be, for example, selected from the group consisting of adenine, guanine and hypoxanthine.

The pyrimidine base can be, for example, selected from the group consisting of thymine, uracile and cytosine, thymine being preferred.

By «non-natural mono- or bicycle heterocyclic base» is meant a universal base, such as, for example, 3-nitropyrrole, 4-nitroimidazole or 5-nitroindole.

By «optionally substituted» is meant that the purine or pyrimidine base, or the non-natural heterocyclic base can be substituted by at least one substituent chosen, for example, from a halogen, an amino group, a carboxy group, a carbonyl group, a carbonylamino group, a hydroxy, azido, cyano, alkyl, cycloalkyl, perfluoroalkyl, alkyloxy (for example, methoxy), oxycarbonyl, vinyl, ethynyl, propynyl, acyl group etc.

«Residue of a cyclic carbohydrate or a derivative of the said carbohydrate» refers to a residue of a 5- or 6-membered osidic cycle, which can be, for instance, selected from D-glucopyranose, D-galactopyranose, D-mannopyranose, D-fructopyranose or D-ribofuranose, or oligosaccharide-type glycans deriving therefrom, as well as their N-acyl derivatives, in particular their N-acetyl derivatives, such as, for instance, N-acetylglucosamine, N-acetylgalactosamine, N-acetylmannosamine or sialic acid, or a protected derivative thereof, such as an O-acyl derivative, in particular an O-acetyl derivative, D-glucopyranose being preferred.

In particular, the invention relates to compounds of formula (I), in which at least one of the following conditions is fulfilled:
n=m=p=1
$R_3$ and $R_5$, identical or different, represent a heteroaryl group containing 1 to 4 nitrogen atoms selected from the group consisting of pyrazole, triazole, tetrazole and imidazole;
$R_4$ represents a nucleosidyl group selected from adenosine, deoxyadenosine, guanosine, deoxyguanosine, thymidine, deoxythymidine, uridine, deoxyuridine, cytidine and deoxycytidine.
$R_6$ represents a residue of a cyclic carbohydrate selected from D-glucopyranose, D-galactopyranose, D-mannopyranose, D-fructopyranose, D-ribofuranose, N-acetylglucosamine, N-acetylgalactosamine, N-acetylmannosamine and sialic acid or a protected derivative thereof.

Preferred compounds of formula (I) are those in which X is oxygen.

Alternatively, compounds of formula (I) of interest are those in which X is —NH—C(O)—NH— or —C(O)—NH—.

Preferred compounds of formula (I) are those in which:
A represents a $C_{12}$ or $C_{14}$ saturated hydrocarbon chain;
$R_1$ is hydrogen, or —$(CH_2)_n$—$R_3$—$(CH_2)_m$—$R_4$—$(CH_2)_p$—$R_5$-$R_6$;
$R_2$ is —$(CH_2)_n$—$R_3$—$(CH_2)_n$—$R_4$—$(CH_2)_p$—$R_5$-$R_6$;
n=m=p=1;
$R_3$ is a triazole group;
$R_4$ is thymidine;
$R_5$ is a triazole group, and
$R_6$ is β-D-glucopyranosyl or 2,3,4,6 tetra-O-protected-glucopyranosyl, preferably 2,3,4,6 tetra-O-acetyl-glucopyranosyl.

Other preferred compounds are those in which
A represents a $C_{10}$ hydrocarbon chain which is partially fluorinated;
$R_1$ and $R_2$ are —$(CH_2)_n$—$R_3$—$(CH_2)_m$—$R_4$—$(CH_2)_p$—$R_5$-$R_6$;
n=m=p=1;
$R_3$ is a triazole group;
$R_4$ is thymidine;
$R_5$ is a triazole group, and
$R_6$ is β-D-glucopyranosyl or 2,3,4,6 tetra-O-protected-glucopyranosyl, preferably 2,3,4,6 tetra-O-acetyl-glucopyranosyl.

According to a preferred embodiment, $R_5$ is covalently linked to $R_4$ via —$(CH_2)p$- to the carbon atom at position 5' of the ribose or deoxyribose ring of the nucleosidyl group.

Alternatively, $R_5$ is covalently linked to $R_4$ via —$(CH_2)p$- to the oxygen atom at position 3' of the ribose or deoxyribose ring of the nucleosidyl group.

Particularly preferred compounds of formula (I) are:
5'-[4-(12-hydroxydodecanyloxy)methyl]-1H-1,2,3-triazol-1-yl]-5'-deoxy-N3-(1-((β-D-glucopyranoside)-1H-1,2,3-triazol-4-yl)methyl thymidine,
1,12-bis-dodecanyl-5'-[(4-oxymethyl)-1H-1,2,3-triazole-1-yl)]-N-3-[1-((β-D-glucopyranoside)-1H-1,2,3-triazole-4-yl)methyl]-5'-deoxy thymidine,
1,12-bis-dodecanyl-5'-[4-(oxymethyl)-1H-1,2,3-triazol-1-yl]-5'-deoxy-3'-O-1-((β-D-glucopyranoside)-1-H-1,2,3-triazol-4-yl)methyl thymidine,
1,10-bis-2,2,3,3,4,4,5,5,6,6,7,7,8,8,9,9-hexafluorodecanyl-5'-[4-(oxymethyl)-1H-1,2,3-triazol-1-yl]-N-3-[1-((β-D-glucopyranoside)-1H-1,2,3-triazol-4-yl)methyl]-5'-deoxythymidine,
1,12-bis-dodecanyl-5'-[(4-methylurea)-1H-1,2,3-triazol-1-yl]-N-3-[1-((2,3,4,6-tetra-O-acetyl-β-D-glucopyranoside)-1H-1,2,3-triazole-4-yl)methyl]-5'-deoxythymidine,
1,12-bis-dodecanyl-5'-[(4-methylurea)-1H-1,2,3-triazol-1-yl]-N-3-[1-((β-D-glucopyranoside)-1H-1,2,3-triazole-4-yl)methyl]-5'-deoxy thymidine,
1,14-bis-tetradecanyl-5'-[(4-methylamide)-1H-1,2,3-triazol-1-yl]-N-3-[1-((2,3,4,6-tetra-O-acetyl-β-D-glucopyranoside)-1H-1,2,3-triazole-4-yl)methyl]-5'-deoxy thymidine, and
1,14-bis-tetradecanyl-5'-[(4-methylamide)-1H-1,2,3-triazol-1-yl]-N-3-[1-((β-D-glucopyranoside)-1H-1,2,3-triazole-4-yl)methyl]-5'-deoxy thymidine.

The compounds of formula (I) in which X is oxygen can be obtained by a process comprising the following steps:
reacting an alkane-diol or a fluoroalkane-diol of formula $R_1$—O-A-O—$R_2$ at both ends with an alkylating agent of formula R—$(CH_2)_q$—C≡CH, where q is 1 or 2 and R is an halide, in particular chloride or bromide,
reacting the resulting compound with the 5'-azido derivative of $R_4$,
reacting the purine or pyrimidine base or universal base moiety of $R_4$ in the resulting compound with an alkylating agent of formula R—$(CH_2)_q$—C≡CH, where q and R are as defined above, in order to obtain the N-alkylated derivative of the purine or pyrimidine base or universal base of $R_4$, and
reacting the resulting compound with the 1-azido derivative of $R_6$ (click-reaction).

In order to obtain compounds of formula (I) in which X is oxygen and $R_3$ and/or $R_5$ are not triazoles, the skilled person is able to choose the appropriate cycloaddition reactions, such as Diels-Alder reactions, in order to obtain the desired $R_3$ and/or $R_5$ heterocycles.

The following reaction conditions are preferred:
the alkylating reactions are performed in the presence of sodium hydride;
the click reaction is carried out with a 1:1 (v/v) mixture of water and dichloromethane with vigorous stirring at 40° C. or a 1:1 (v/v) mixture of water and THF at 60-65° C. with 10% CuSO$_4$ and 20% ascorbic acid;

If desired, the synthesis of unsymmetrical compounds of formula (I) where one of R$_1$ and R$_2$ represents hydrogen and the other is —(CH$_2$)$_n$—R$_3$—(CH$_2$)$_m$—R$_4$-(CH$_2$)$_p$—R$_5$-R$_6$ can be undertaken starting with monoalkylated starting materials clicked with the 5'-azido derivative of R$_4$. Subsequent reaction of the purine or pyrimidine base moiety present in the resulting compound with an alkylating agent of formula R—CH$_2$—C≡CH followed by a second click reaction with the 1-azido derivative of R$_6$ affords the desired unsymmetrical compound of formula (I).

The compounds of formula (I) in which X is —NH—C(O)—NH— (bis-urea compounds) can be obtained by a process comprising the following steps:
reacting a diisocyanatoalkane of formula OCN-A-NCO with NH$_2$—CH$_2$—C≡CH (propargylamine) or any primary amine containing a terminal alkyne group) in order to obtain a compound of formula (II)

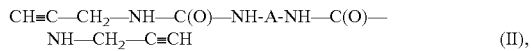

CH≡C—CH$_2$—NH—C(O)—NH-A-NH—C(O)—NH—CH$_2$—C≡CH          (II), reacting a purine or pyrimidine base or a universal base with an alkylating agent of formula R—(CH$_2$)$_q$—C≡CH, where q is 1 or 2 and R is an halide, preferably bromide or chlorine, in order to obtain the N-alkylated derivative of the purine or pyrimidine base or universal base of R$_4$,
reacting the resulting compound with the 1-azido derivative of R$_6$ (click-reaction),
converting the 5'—OH group on the ribose or deoxyribose moiety of R$_4$ into an azide, and subjecting the resulting compound to a second click-reaction with a compound of formula (II).

The following reaction conditions are preferred:
the alkylating reaction of the purine or pyrimidine base or universal base with R—CH$_2$—C≡CH is carried out under basic conditions;
the first click-reaction is Cu(I) catalyzed and is carried out in a 1:1 (v/v) mixture of water and tert-butanol, preferably at 60° C., and preferably with 10% CuSO$_4$ and 20% ascorbic acid;
the conversion of the 5'—OH group on the ribose or deoxyribose moiety of R$_4$ into an azide can be carried out by using an organophosphorous compound, such as, for example, triphenylphosphine (PPh$_3$), a carbon halide such as, for example, tetrabromide (CBr$_4$) and sodium azide (NaN$_3$).

The compounds of formula (I) in which X is —C(O)—NH— (bis-amide compounds) can be obtained by a process comprising the following steps:
reacting an alkane diacid chloride prepared in situ from the corresponding dicarboxylic acid of formula HOOC-A-COOH and thionyl chloride, with NH$_2$—CH$_2$—C≡CH (propargylamine) or any primary amine containing a terminal alkyne group in order to obtain a compound of formula (III)

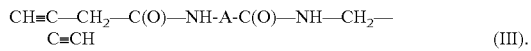

CH≡C—CH$_2$—C(O)—NH-A-C(O)—NH—CH$_2$—C≡CH          (III).

The following steps are the same are those described above for obtaining bis-urea compounds of formula (I).

The invention further relates to compounds of formula (IV)

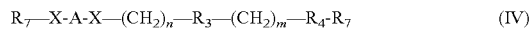

R$_7$—X-A-X—(CH$_2$)$_n$—R$_3$—(CH$_2$)$_m$—R$_4$-R$_7$          (IV)

In which
X is —NH—C(O)—NH—;
A is a C$_4$-C$_{30}$ hydrocarbon chain, linear or branched, saturated or unsaturated, which is unsubstituted or substituted by one or more C$_1$-C$_{12}$ linear or branched alkyl groups, or A represents a C$_4$-C$_{30}$ hydrocarbon chain, linear or branched, saturated or unsaturated, which is partially or completely halogenated;
R$_3$ represents a heteroaryl group comprising 1 to 4 oxygen or nitrogen atom(s);
R$_4$ represents a nucleosidyl group;
R$_7$ is the residue of an alkylating agent of formula R—(CH$_2$)$_q$—C≡CH where q is 1 or 2 and R is an halide, which is linked by a covalent bond with a nitrogen atom of the purine, pyrimidine or universal base moiety of R$_4$;
n and m, identical or different, are 0 to 10.

R is preferably chloride or bromide, and q is preferably 1.
The compounds of formula (IV) are useful as synthesis intermediates for obtaining the compounds of formula (I) in which X is oxygen.

All the preferred features mentioned above for A, R$_3$ and R$_4$ in formula (I) also apply to formula (IV).

Preferred compounds of formula (IV) are those in which
n=m=1
R$_3$ is a triazole group;
R$_4$ is thymidine;
R$_7$ is propargyl.

In particular, compounds of formula (IV) of interest are:
5'-[4-((12-Propargyloxydodecanyloxy)methyl)-1H-1,2,3-triazol-1-yl]-5'-deoxy-N-3-propargylthymidine,
1,12-bis-dodecanyl-5'-[(4-oxymethyl)-1H-1,2,3-triazol-1-yl)]-5'-deoxy-N-3-propargyl thymidine, and
1,10-bis-2,2,3,3,4,4,5,5,6,6,7,7,8,8,9,9-hexafluorodecanyl-5'-[4-(oxymethyl)-1H-1,2,3-triazol-1-yl]-N-3-propargyl-5'-deoxythymidine.

The invention further relates to compounds of formula (V)

R$_4$—(CH$_2$)$_p$—R$_5$-R$_6$          (V)

In which
R$_4$ represents a nucleosidyl group;
R$_5$ represents a heteroaryl group comprising 1 to 4 heteroatom(s), which is linked to R$_4$ by a covalent bond to a nitrogen atom of the pyrimidine base or of the purine base of the nucleosidyl group;
R$_6$ represents a residue of a cyclic carbohydrate or a derivative of the said carbohydrate, which is optionally substituted;
p is 0 to 10.
Preferably, R$_4$ is a triazole group.
Preferably, R$_5$ is thymidinyl, and R$_4$ is linked to the nitrogen in position 3 of R$_5$.

By «optionally substituted» is meant that the cyclic carbohydrate or derivative thereof can be substituted by at least one substituent chosen, for example, from a halogen, an amino group, a carboxy group, a carbonyl group, a carbonylamino group, a hydroxy, azido, cyano, alkyl, cycloalkyl, perfluoroalkyl, alkyloxy (for example, methoxy), oxycarbonyl, vinyl, ethynyl, propynyl, acyl group etc.

The compounds of formula (V) are useful as synthesis intermediates for obtaining the compounds of formula (I) in which X is —NH—C(O)—NH— or —C(O)—NH—.

All the preferred features mentioned above for $R_4$, $R_5$ and $R_7$ in formula (I) also apply to formula (V).

Preferred compounds of formula (V) are those in which
p=1
$R_3$ is a triazole group;
$R_5$ is thymidine or
$R_6$ is a residue of 2,3,4,6 tetra-O-protected-glucopyranosyl.

In particular, compounds of formula (V) of interest are:
5'-deoxy-N3-(1-(2,3,4,6-tetra-O-acetyl-β-D-glucopyranoside)-1H-1,2,3-triazol-4-yl) thymidine, and
5'-Azido-N3-(1-(2,3,4,6-tetra-O-acetyl-β-D-glucopyranoside)-1H-1,2,3-triazol-4-yl) thymidine.

The invention also relates to biocompatible hydrogels formed from at least one compound of formula (I). In particular, these hydrogels are formed from an aqueous solution of compounds of formula (I) which can contain, for example, 0.1 to 10 wt % of compound of formula (I), in particular 1 to 5 wt %.

The biocompatible hydrogels according to the invention can comprise one or more compound(s) of formula (I), or a mixture of one or more compound(s) of formula (I) and one or more glycosyl-nucleoside(s)-lipid(s) (also called GNL) and/or glycosyl-nucleoside(s)-fluorolipid(s) (also called GNF).

The biocompatible hydrogels according to the invention can also contain a mixture of one or more compound(s) of formula (I) with one or more protein(s) or glycoprotein(s), such as for example collagen or hyaluronic acid, and optionally, one or more GNL or GNF.

"Biocompatible" is understood as a material which is well tolerated by the host organism and which does not cause any rejection, toxic reaction, injury or harmful effect on the biological functions of the host organism.

The biocompatible hydrogels according to the invention can be prepared, for example, by hating the compounds of formula (I) until dissolution, for example at a temperature of 40° C. to 50° C., and allowing the solution to cool gradually to room temperature.

All the preferred features mentioned above for the compounds of formula (I) also apply to the hydrogels formed therefrom.

The invention also relates to the use of hydrogels formed from compounds of formula (I) as cell culture media, in particular as culture media for animal or human cells.

The hydrogels according to the invention are particularly suitable as culture media for eukaryotic cells, in particular for stem cell culture. Indeed, it has been surprisingly found that these hydrogels allow the culture of stem cells under isolated form, while when using existing LMWG, such as those formed from GNF, formation of clusters of stem cells was observed. The culture of isolated eukaryotic cells, in particular stem cells, is highly valuable and promising in view of the extensive research which is currently carried out on stem cells. Advantageously, the hydrogels formed from compounds of formula (I) possess particular viscoelastic properties. Indeed, rheological studies on the variation of the storage modulus G' (also called elastic modulus) and the loss modulus G" (also called viscous modulus) as a function of the applied frequency were performed. G' describes the amount of energy which is stored and released in each oscillation, and G" corresponds to the energy which is dissipated at heat. Surprisingly, it has been found that the storage modulus G' is higher than the loss modulus G", which indicates the formation of a stable gel. Without wishing to be bound by theory, it can be hypothesized that this high elastic modulus plays a role in the adhesion and proliferation of isolated stem cells.

In addition, it has been found that the hydrogel formed from compounds of formula (I) possess a thixotropic behaviour, and thus can be delivered by a syringe, thus allowing surgical use. Actually, said hydrogel is able to regain its gel behaviour and strength after a high strain is applied thereto.

In particular, the hydrogel according to the invention can be used as biocompatible materials in the following biomedical applications:

Tissue engineering, for instance by injecting gel-cell complexes: which can be used, for example, for bone regeneration;

Cellular therapy, for instance by injecting gel-cell complexes in which the cells produce the active molecule(s)

Prevention of adhesion formation after abdomino-pelvic surgery, for instance by injecting the gel which will remain at the application location and act as a barrier between adjacent tissues.

Also, the biocompatible hydrogel according to the invention can be used as biocompatible material for drug delivery, for instance:

for controlled-release delivery of an active ingredient which is entrapped into the gel, allowing the active ingredient to diffuse slowly near the injection site (topical administration, such as, for instance, for chemotherapy) and/or in the blood flow;

for hosting delivery devices, such as, for instance for the encapsulation of electrically stimulable devices.

The invention is non limitatively supported by the examples below.

All commercially available reagents and solvents (Fluka, Sigma-Aldrich, Alfa-Aesar) were used without further purification.

For reactions requiring anhydrous conditions, dry solvents were used (Sigma-Aldrich) under inert atmosphere (nitrogen or argon).

Analytical thin layer chromatography (TLC) was performed on pre-coated silica gel $F_{254}$ plates with fluorescent indicator (Merck). The detection of compounds was accomplished with UV light (254 nm) and by subsequent spraying with 10% conc. $H_2SO_4$ solution in ethanol, followed by heating, or 1% aqueous $KMnO_4$ followed by heating.

Column chromatography was performed with flash silica gel (0.04-0.063 mm, Merck) or with ready-to-use Chromabon RS 40 flash chromatography columns (Macherey-Nagel). All compounds were characterized using $^1H$ and $^{13}C$ Nuclear Magnetic Resonance (NMR) spectroscopy (Bruker Avance DPX-300 spectrometer, $^1H$ at 300.13 MHz and $^{13}C$ at 75.46 MHz). Assignments were made by $^1H$-$^1H$ COSY, DEPT and HSQC experiments. Chemical shifts (δ) are given in parts per million (ppm) relatively to tetramethylsilane or residual solvent peaks ($CHCl_3$: $^1H$: 7.26, $^{13}C$: 77.0). Coupling constants J are given in Hertz (Hz); peak multiplicity is reported as follows: s=singlet, bs=broad singlet, d=doublet, t=triplet, m=multiplet.

High resolution electrospray ionization mass spectra (HR ESI-MS) were performed by the CESAMO (Bordeaux, France) on a QSsat Elite mass spectrometer (Applied Biosystems). The instrument is equipped with an ESI source and spectra were recorded in negative mode. The electrospray needle was maintained at 4500 V and operated at room temperature. Samples were introduced by injection through a 10 μL sample loop into a 200 μL/min flow of methanol from the LC pump.

The following abbreviations are used:
DCM dichloromethane
DMF dimethylformamide
DMSO dimethylsulfoxide
TBAI tetrabutylammonium iodide
THF tetrahydrofuran The examples below, entitled "Preparation" describe the preparation of synthesis intermediates used for preparing the compounds of formula (I). The preparation of the compounds of formula (I) and their applications are then described as "Examples". When present, the number that accompanies the title compound in the "Preparation" or in the "Example" refers to that shown in the schemes of FIGS. 1, 2 and 3.

Figure 8:
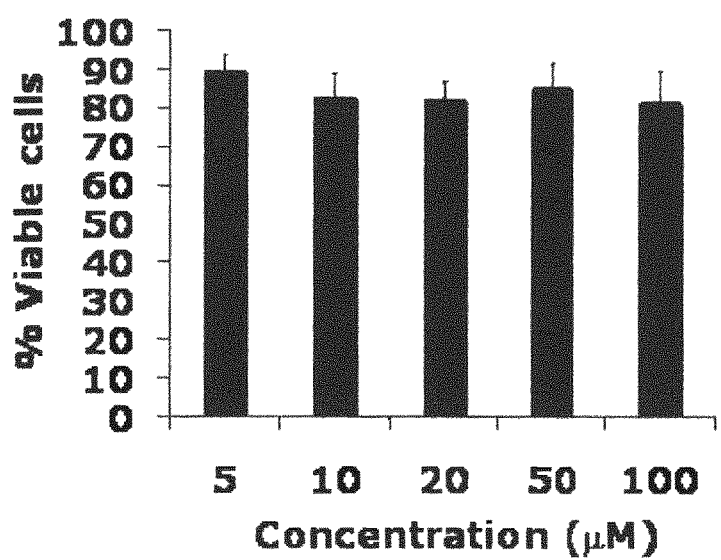

FIG. 8 shows the cytotoxycity of compound GNL of G. Godeau et al., Chem. Comm., 2009, 34, 5127-5130_by MTT test in human hepatic carcinoma cells HuH-7 (comparative example).

PREPARATION 1

1,12-Dipropargyloxydecane (2)

To a cooled (0° C.) solution of compound 1 (commercially available) (5 g, 24.7 mmol) in anhydrous DMF (60 mL) was added sodium hydride in small portions (55% in mineral oil, 6.5 g, 148.2 mmol) under stirring. Propargyl bromide (80% w/w in toluene, 11 g, 74.1 mmol) was added followed by TBAI (0.91 g, 2.4 mmol), and stirring was continued for 15 hours at room temperature. The reaction was quenched with methanol (10 mL) and stirred a further 30 min. After addition of DCM (200 mL) the solution was washed with water (3×50 mL) then brine (50 mL), the organic layer dried ($Na_2SO_4$) and concentrated under reduced pressure. Product 2 was isolated after purification on silica gel (hexane/ethyl acetate 100/0 then 97/3) as a colorless liquid. Yield: 4.48 g (65%).

$^1$H NMR (300 MHz, in $CDCl_3$) δ 1.22-1.43 (m, 16H, $CH_2$), 1.52-1.66 (m, 4H, $CH_2CH_2O$), 2.43 (t, J=2.4 Hz, 2H, CH propargyl), 3.52 (t, J=6.6 Hz, 4H, $CH_2CH_2O$), 4.15 (d, J=2.4 Hz, 4H, $CH_2$ propargyl).

$^{13}$C NMR (75 MHz, in $CDCl_3$) δ 26.08, 29.42, 29.50, 29.55 ($CH_2$, $CH_2CH_2$O), 57.97 ($CH_2$ propargyl), 70.31 ($CH_2O$), 74.01 (CH propargyl).

PREPARATION 2

12-Propargyloxydodecan-1-ol (7)

To a cooled (0° C.) solution of compound 1 (commercially available) (4 g, 20 mmol) in anhydrous DMF (100 mL) was added sodium hydride in small portions (55% in mineral oil, 2.5 g, 109 mmol) under stirring. Propargyl bromide (80% w/w in toluene, 9 g, 60 mmol) was added dropwise, and stirring was continued for 12 hours at low temperature. The reaction mixture was concentrated under reduced pressure. The resulting mixture was poured into water and extracted with DCM. The extracts were combined, washed with water (3×50 mL) then brine (50 mL). The organic layer was dried ($Na_2SO_4$) and concentrated under reduced pressure. Product 7 was isolated after purification on silica gel (hexane/ethyl acetate 6/4) as a brown solid. Yield: 2.24 g (46%).

$^1$H NMR (300 MHz, in $CDCl_3$) δ 1.19-1.30 (m, 16H, $CH_2$), 1.46-1.59 (m, 4H, $CH_2CH_2O$), 2.37 (large s, 1H, OH), 2.40 (t, J=2.4 Hz, 1H, CH propargyl), 3.46 (t, J=6.6 Hz, 2H, $CH_2O$), 3.56 (t, J=6.7 Hz, 2H, $CH_2O$), 4.08 (d, J=2.4 Hz, $CH_2$ propargyl).

$^{13}$C NMR (75 MHz, in $CDCl_3$) δ 25.74, 26.03 ($CH_2$), 29.39, 29.43, 29.53, 29.58 ($CH_2$+$CH_2OH_2O$), 32.70 ($CH_2CH_2O$), 57.92 ($CH_2$ propargyl), 62.72, 70.22 ($CH_2O$), 74.13 (CH propargyl).

PREPARATION 3

1,12-bis-dodecanyl-5'-[(4-oxymethyl)-1H-1,2,3-triazol-1-yl)]-5'-deoxy thymidine (3)

To a solution of 7 obtained in Preparation 2 (1.50 g, 5.39 mmol) and 5'-azido-5'-deoxythymidine (3.02 g, 11.30 mmol) in 140 mL of THF/$H_2O$ (1:1) was added copper sulfate (172 mg, 1.07 mmol) followed by sodium ascorbate (427 mg, 2.15 mmol). The mixture was stirred at 60° C. for 20 hours. After cooling to room temperature, the solvents were removed under reduced pressure. The resulting solid was washed with water until the washings were colorless, and then with ethanol. After drying under high vacuum, the resulting white solid was used in the next step without further purification. Yield: 4.00 g (91%).

$^1$H NMR (300 MHz, in DMSO-$d_6$) δ 1.22 (s, 16H, 8$OH_2$), 1.41-1.52 (m, 4H, $CH_2CH_2O$), 1.79 (s, 6H, $CH_3$ thymine), 2.08-2.15 (m, 4H, H-2'), 3.35-3.41 (m, 4H, $CH_2O$), 4.06-4.10 (m, 2H, H-4'), 4.24-4.29 (m, 2H, H-3'), 4.27 (s, 4H, O$CH_2$-triazole), 4.57-4.74 (m, 4H, H-5'), 5.52 large s, 2H, OH thymine), 6.16 (t, J=7.5 Hz, 2H, H-1'), 7.33 (s, 2H, H-6 thymine), 8.06 (s, 2H, CH triazole), 11.34 (s, 2H, NH thymine).

$^{13}$C NMR (75 MHz, in DMSO-$d_6$) δ 12.53 ($CH_3$ thymine), 6.11, 29.33, 29.48, 29.55 ($CH_2$), 38.31 (C-2'), 51.51 (C-5'), 63.68 ($CH_2$O-triazole), 70.01 ($CH_2O$), 71.16 (C-3'), 84.40 (O1' and C-4'), 125.00 (CH triazole), 136.45 (C-6 thymine).

PREPARATION 4

1,12-bis-dodecanyl-5'-[(4-oxymethyl)-1H-1,2,3-triazol-1-yl)]-5'-deoxy-N-3-propargyl thymidine (4)

To as solution of compound 3 obtained in Preparation 3 (3.50 g, 4.30 mmol) in anhydrous DMF (120 mL) was added sodium carbonate (1.7 g, 12.92 mmol) followed by propargyl bromide (80% w/w in toluene, 1.92 g, 12.92 mmol) and TBAI (0.16 g, 043 mmol). The mixture was stirred at room temperature for 20 hours, then poured into DCM (200 mL) and washed with water (3×50 mL) and brine (50 mL). The organic extract was dried ($Na_2SO_4$) and concentrated under reduced pressure. The product was purified by column chromatography on silica gel eluting with DCM/MeOH (100:0 to 96:4) and obtained as a white solid foam. Yield: 3.07 g (77%).

$^1$H NMR (300 MHz, in $CDCl_3$) δ 1.27 (s, 16H, 8 $CH_2$), 1.53-1.60 (m, 4H, 2 $CH_2CH_2O$), 1.94 (s, 6H, 2 $CH_3$ thymine), 2.22 (t, 2H, J=2.3 Hz, propargylic CH), 2.31-2.41 (m, 4H, 2H-2'), 3.52 (t, 4H, J=6.5 Hz, 2 $CH_2O$), 4.23-4.27 (m, 2H, 2H-4'), 4.53-4.59 (m, 2H, 2H-3'), 4.61 (s, 4H, 2 $CH_2O$ triazole), 4.71 (s, 4H, 2 propargylic $CH_2$), 4.70-4.77 (m, 4H, 2H-5'), 6.23 (t, 2H, J=6.6 Hz, 2H-1'), 6.81 (s, 2H, 2H-6 thymine), 7.68 (s, 2H, 2H triazole).

$^{13}$C NMR (75 MHz, in $CDCl_3$) δ 13.16 ($CH_3$ thymine), 29.22, 29.31, 29.34, 29.47 ($CH_2$), 30.50 (propargyl $CH_2$), 38.61 (C-2'), 51.11 (C-5'), 63.93 ($OCH_2$ triazole), 71.14 ($CH_2O$), 71.23 (C-3'), 77.25 (propargyl CH), 83.79 (C-4'), 86.85 (C-1'), 124.60 (CH triazole), 134.72 (C-6 thymine).

PREPARATION 5

5'-[4-((12-Hydroxydodecanyloxy)methyl)1H-1,2,3-triazol-1-yl]-5'-deoxy thymidine (8)

To a degassed solution of compound 7 obtained in Preparation 1 (2.23 g, 9.30 mmol) in 80 mL $THF/H_2O$ (1:1) was added 5'-azido-5'-deoxy thymidine (2.48 g, 9.30 mmol), copper sulfate (0.15 g, 0.93 mmol) and sodium ascorbate (0.37 g, 1.86 mmol). The mixture was stirred at 60° C. for 3 hours. After removal of THF in vacuo, the aqueous mixture was filtered, the resulting yellow solid was washed with water, then purified by column chromatography on silica gel eluting with DCM/MeOH (9:1) to elute the product as a white solid. Yield: 3.88 g (82%).

$^1$H NMR (300 MHz, in MeOD @ 313K) δ 1.30-1.39 (m, 16H, $CH_2$), 1.52-1.60 (m, 4H, $CH_2CH_2O$), 1.89 (d, J=1.2 Hz, 3H, $CH_3$ thymine), 2.23-2.29 (m, 2H, H-2'), 3.49-3.57 (m, 4H chain $CH_2O+CH_2OH$), 4.16-4.21 (m, 1H, H-4'), 4.39-4.43 (m, 1H, H-3'), 4.72-4.81 (m, 2H, H-5'), 6.20 (t, J=6.7 Hz, H-1'), 7.20 (d, 1H, H-6 thymine), 7.95 (s, 1H, CH triazole).

$^{13}$C NMR (75 MHz, in MeOD @ 313K) δ 10.95 ($CH_3$ thymine), 25.51, 25.74, 29.06, 29.13, 29.22, 29.27, 32.25 ($CH_2$), 38.26 (C-2'), 51.09 (C-5'), 61.64 ($CH_2OH$ or $CH_2CH_2O$), 63.27 ($CH_2O$ triazole), 70.38 ($CH_2CH_2O$ or $CH_2OH$), 70.98 (C-3'), 84.06 (C-4'), 85.46 (C-1'), 110.10 (C-5 thymine), 124.61 (CH triazole), 136.55 (C-6 thymine), 150.30 & 164.31 (C=O).

HRMS: (M+Na) 530.2943 (calculated 530.2949)

PREPARATION 6

5'-[4-((12-Hydroxydodecanyloxy)methyl)-1H-1,2,3-triazol-1-yl]-5'deoxy-N-3-propargylthymidine (9)

To a solution of compound 8 obtained in Preparation 5 (1.27 g, 25.0 mmol) in anhydrous DMF (60 mL) was added potassium carbonate (0.69 g, 50.0 mmol) and TBAI (0.09 g, 2.5 mmol), followed by propargyl bromide (80% w/w in toluene, 1.19 g, 50.0 mmol). The mixture was stirred at room temperature for 24 hours, then filtered, and the filtrate was concentrated under reduced pressure. The resulting yellow oil was poured into water (50 mL) and extracted with DCM (3×50 mL). The combined organic extracts were washed with water (50 mL), then brine (50 mL), dried ($Na_2SO_4$), and the solvent removed in vacuo. The crude product was purified by column chromatography on silica gel eluting with DCM/MeOH (95:5) to elute the title compound as a viscous yellow oil which crystallizes on standing (white solid). Yield: 1.20 g (87%).

$^1$H NMR (300 MHz, in $CDCl_3$) δ 1.26-1.34 (m, 16H, $CH_2$), 1.51-1.62 (m, 4H, $CH_2CH_2OH+CH_2CH_2O$), 1.93 (d, J=1.1 Hz, 3H, $CH_3$ thymine), 2.20 (t, J=2.4 Hz, 1H, propagylic CH), 2.22-2.29 (m, 1H, H-2'a), 2.35-2.44 (m, 1H, H-2'b), 3.48-3.56 (m, 2H $CH_2O$), 3.65 (t, J=6.6 Hz, 2H, $CH_2OH$), 4.18-4.23 (m, 1H, H-4'), 4.45-4.51 (m, 1H, H-3'), 4.59 (s, 2H triazole $CH_2O$), 4.70-4.74 (m, 4H, H-5'+propargylic $CH_2$), 6.25 (t, J=6.6 Hz, H-1'), 6.74 (d, 1H, H-6 thymine), 7.68 (s, 1H, CH triazole).

$^{13}$C NMR (75 MHz, in $CDCl_3$) δ 12.93 ($CH_3$ thymine), 25.68, 25.91, 29.30, 29.33, 29.41, 29.47 ($CH_2+CH_2OH_2OH$ or $CH_2OH_2O$), 30.36 (propargylic $CH_2$), 32.55 ($CH_2OH_2O$ or $CH_2OH_2OH$), 38.58 (C-2'), 51.00 (C-5'), 62.49 ($CH_2OH$), 63.85 ($CH_2$ triazole), 70.65 (C-3'), 70.85 (propargylic CH), 70.99 (triazole $CH_2O$), 83.77 (C-4'), 86.30 (C-1'), 124.48 (CH triazole), 134.83 (C-6 thymine).

HRMS: (M+Na) 568.3098 (calculated 568.3105)

PREPARATION 7

5'-[4-((12-Propargyloxydodecanyloxy)methyl)-1H-1,2,3-triazol-1-yl]-5'-deoxy-N-3-propargylthymidine (10)

To a cold (0° C.) solution of compound 8 obtained in Preparation 5 (2 g, 3.66 mmol) in anhydrous DMF (100 mL) was added sodium hydride in one portion (55% in mineral oil, 0.90 g, 22 mmol). After 15 min, TBAI (0.135 g, 0.36 mmol) was added followed by propargyl bromide in small portions (80% w/w in toluene, 1.63 g, 11 mmol), and stirring continued for 5 hours at 0° then at room temperature overnight. The reaction was quenched with water (10 mL) with stirring and cooling on ice, and the solution was concentrated under reduced pressure. The brown residue was dissolved in water (200 mL) and extracted with DCM (3×100 mL) The combined organic extracts were washed with brine (3×100 mL) and aqueous 10% KCl solution (100 mL), dried ($Na_2SO_4$) and the solvent removed in vacuo. The crude product was purified by chromatography on silica gel eluting with ethyl acetate and obtained as a yellow oil. Yield: 0.87 g (40%).

$^1$H NMR (300 MHz, in $CDCl_3$) δ 1.23-1.27 (m, 16H, $CH_2$), 1.48-1.56 (m, 4H, $CH_2OH_2O$), 1.89 (s, 3H, $CH_3$ thymine), 2.08-2.17 (m, 1H, H-2'a), 2.18 (m, 1H thymine propagylic CH), 2.35-2.43 (m, 1H, H-2'b), 2.51 (m, 1H, chain propargylic CH), 3.48 (t, J=6.7 Hz, 2H $CH_2OCH_2$-triazole), 3.59 (t, J=6.6 Hz, 2H, chain $CH_2O$-propargyl), 4.17-4.20 (m, 2H, propargylic $CH_2O$), 4.24-4.30 (m, 1H, H-4'), 4.35-4.40 (m, 1H, H-3'), 4.57 (s, 2H $CH_2$ triazole), 4.57-4.70 (m, 4H, H-5'+propargylic $CH_2N$), 6.14 (t, J=6.9 Hz, H-1'), 6.73 (s, 1H, H-6 thymine), 7.62 (s, 1H, CH triazole).

$^{13}$C NMR (75 MHz, in $CDCl_3$) δ 13.06 ($CH_3$ thymine), 25.73, 26.03, 29.49, 29.54 ($CH_2$), 29.39 ($CH_2CH_2O$), 30.42 (thymine propargylic $CH_2$), 32.76 ($CH_2CH_2O$ propargyl), 36.23 (C-2'), 50.92 (C-5'), 57.41 (propargylic $CH_2O$), 62.84 (chain $CH_2O$-propargyl), 64.16 ($CH_2$ triazole), 70.80 (thymine propargylic CH), 71.08 (chain $CH_2OCH_2$ triazole), 75.70 (chain propargylic CH), 78.26 (C-3'), 81.76 (C-4'), 86.69 (C-1'), 124.18 (CH triazole), 134.30 (C-6 thymine).

HRMS: (M+Na) 606.3258 (calculated 606.3262)

PREPARATION 8

1,1'-(dodecane-1,12-diyl)bis(3-[propargyl]urea) (12)

To a solution of 1,12-diisocyanatododecane (0.53 mL, 2 mmol) in anhydrous DCM (20 mL) was added slowly propargylamine (0.30 mL, 4.8 mmol). The mixture was stirred for 16 hours at room temperature. The precipitate was filtered and washed abundantly with DCM to remove the excess of propargylamine. After drying, the product was obtained as a white solid.

Yield: (99%).

$^1$H NMR (300 MHz, in DMSO-d$_6$ @350 K) δ (ppm) 1.50-1.63 (m, 20H), 3.15 (t, J=2.6 Hz, 2H), 3.20-3.26 (q, 4H), 4.03 (m, J=2.6 Hz, 4H), 6.08-6.25 (large s, 4H).

$^{13}$C NMR (75 MHz, DMSO-d$_6$, 350 K) δ (ppm) 26.82, 27.91, 28.05, 29.26, 29.32, 29.69, 30.34, 31.0, 31.09, 72.58, 83.05, 158.02.

PREPARATION 9

N3-propargylthymidine (13)

To a solution of thymidine (3 g, 12.39 mmol) in anhydrous DMF (20 mL) was added potassium carbonate (2.58 g, 18.58 mmol), propargyl bromide (80% w/w in toluene, 2.07 mL, 18.58 mmol). The reaction was stirred for 2 days at room temperature. After removal of DMF in vacuo, the residue was dissolved in ethyl acetate (100 mL) and then washed with water (3×30 mL). The organic extract was dried (Na$_2$SO$_4$) and concentrated under reduced pressure. The resulting oil was used in the next step without further purification. Yield: 3 g (86%).

$^1$H NMR (300 MHz, in DMSO d$_6$) δ 1.85 (s, 3H), 2.10-2.18 (m, 2H), 3.10 (s, 1H), 3.59 (m, 2H), 3.79 (s, 1H), 4.25 (m, 1H), 4.53 (s, 2H), 5.04 (t, J=6 Hz, 1H), 5.27 (s, 1H), 6.21 (t, J=6 Hz, 1H), 7.82 (s, 1H).

$^{13}$C NMR (75 MHz, in DMSO d$_6$) δ 13.0, 30.3, 40.3, 62.0, 70.9, 71.1, 78.2, 86.0, 87.1, 116.9, 135.2, 150.2, 162.7.

HRMS: (M+H) 281, 1135 (calculated 281.1137)

PREPARATION 10

Compound (14)

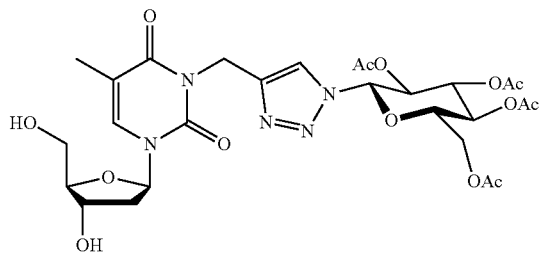

5'-deoxy-N3-(1-(2,3,4,6-tetra-O-acetyl-β-D-glucopyranoside)-1H-1,2,3-triazol-4-yl) thymidine (14)

To a solution of 13 obtained in Preparation 9 (2.80 g, 10 mmol) and 2,3,4,6-tetra-O-acetyl-β-D-glucopyranosyl azide (3.73 g, 10 mmol) in 80 mL of tert-butanol/H$_2$O (1:1) was added copper sulfate (159 mg, 1 mmol) and sodium ascorbate (396 mg, 2 mmol). The mixture was stirred at 60° C. for 20 hours. The solvent was removed under reduced pressure and the residual solid was dissolved in ethyl acetate (150 mL) and then washed with water (3×50 mL). The organic extract was dried (Na$_2$SO$_4$) and concentrated under reduced pressure. The crude product was purified by chromatography on silica gel eluting with ethyl acetate and obtained as a white solid. Yield: 5.33 g (82%).

$^1$H NMR (300 MHz, in CDCl$_3$) δ 1.84-2.08 (m, 15H), 2.35 (m, 2H), 3.82-3.92 (m, 2H), 4.00 (m, 2H), 4.11-4.15 (dd, 1H), 4.25-4.31 (dd, 1H), 4.58 (m, 1H), 5.19-5.31 (m, 3H), 5.36-5.48 (m, 2H), 5.85 (d, J=8.8 Hz, 1H), 6.23 (t, J=6.4 Hz, 1H), 7.52 (s, 1H), 7.88 (s, 1H).

$^{13}$C NMR (75 MHz, in CDCl$_3$) δ 12.47, 19.93, 20.32, 20.47, 35.18, 39.60, 61.00, 61.22, 67.03, 69.58, 70.15, 72.03, 74.14, 84.72, 85.45, 86.62, 99.37, 109.15, 122.30, 134.58, 142.94, 149.97, 162.53, 168.23, 168.77, 169.22, 169.99.

PREPARATION 11

Compound (15)

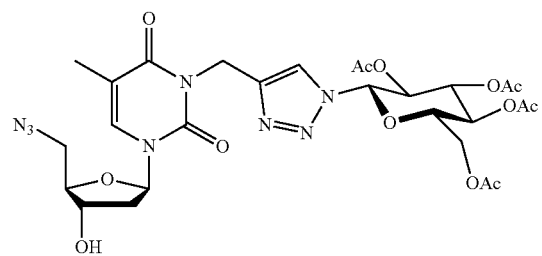

5'-Azido-N3-(1-(2,3,4,6-tetra-O-acetyl-β-D-glucopyranoside)-1H-1,2,3-triazol-4-yl) thymidine (15)

To a solution of 14 obtained in Preparation 10 (1 g, 1.53 mmol) in anhydrous DMF (6 mL) was successively added PPh$_3$ (0.48 g, 1.84 mmol), NaN$_3$ (0.50 g, 7.65 mmol) and CBr$_4$ (0.61 g, 1.84 mmol). After stirring for 24 hours, the reaction was quenched with methanol (1.5 mL) and stirred a further 30 min. The solvent was removed under reduced pressure and the product was isolated after purification on silica gel (DCM/MeOH 100/0 then 97/3) as a white solid. Yield: 1.31 g (77%).

$^1$H NMR (300 MHz, in CDCl$_3$) δ 1.72-1.97 (m, 15H), 2.10-2.17 (m, 1H), 2.30-2.33 (m, 1H), 3.49-3.65 (m, 2H), 4.00-4.22 (m, 3H), 4.25-4.31 (dd, 1H), 4.38 (m, 1H), 5.05-5.22 (m, 3H), 5.35-5.45 (m, 2H), 5.85 (d, J=8.8 Hz, 1H), 6.23 (t, J=6.4 Hz, 1H), 7.33 (s, 1H), 7.85 (s, 1H).

$^{13}$C NMR (75 MHz, in CDCl$_3$) δ 12.47, 19.98-20.53, 35.76, 39.97, 52.09, 61.50, 67.56, 70.06, 71.07, 72.58, 74.72, 84.44, 85.32, 110.17, 122.68, 134.04, 143.49, 150.44, 162.87, 168.68, 170.50.

PREPARATION 12

1,1'-(tetradecane-1,14-diyl)bis(3-[propargyl]amide) (18)

Thionyl chloride (9.12 mmol, 2.1 eq) and triethylamine (13.02 mmol, 3 eq) was added dropwise to a suspension of hexadecanedioic acid (4.34 mmol) in dry DCM. The mixture was vigorously stirred for 1 hour at room temperature. Then, propargylamine (9.55 mmol, 2.2 eq) was added slowly. After stirring for 16 hours, the mixture was filtrated and the crude product was washed abundantly with water and ethanol. Yield: 36%.

$^1$H NMR (300 MHz, DMSO-d$_6$, 340 K) δ 1.25-1.49 (m, 24H), 2.08 (t, 4H), 2.93 (t, 2H), 3.83 (m, 4H), 7.99 (large s, 4H).

$^{13}$C NMR (75 MHz, DMSO-d$_6$, 340 K) δ 24.6, 27.3, 28.2, 28.3, 28.4, 28.5, 34.7, 71.9, 81.0, 171.5.

Example 1

5'-[4-(12-hydroxydodecanyloxy)methyl)-1H-1,2,3-triazol-1-yl]-5'-deoxy-N3-(1-((β-D-glucopyranoside)-1H-1,2,3-triazol-4-yl)methyl thymidine (5)

To a degassed solution of compound 9 obtained in Preparation 6 (1.182 g, 2.0 mmol) and 1-azido-β-D-glucopyranose (0.534 g, 2.0 mmol) in 20 mL of THF/H$_2$O (1:1) was added copper sulfate (32 mg, 0.2 mmol) followed by sodium ascorbate (80 mg, 0.4 mmol). The mixture was stirred at 60° C. for 20 hours. After cooling to room temperature, the solvents were removed under reduced pressure. The resulting green solid was dissolved in methanol and filtered through celite, the resulting solution was concentrated under reduced pressure and applied to a column of silica gel. The product was eluted with DCM/MeOH (9:1 to 8:2). Yield: 0.84 g (55%).

$^1$H NMR (300 MHz, in MeOD) δ 1.28-1.35 (s, 18H, CH$_2$), 1.51-1.60 (m, 4H, CH$_2$CH$_2$O), 1.94 (s, 3H, CH$_3$ thymine), 2.28-2.32 (dd, J=6.0 Hz, 2H, H-2'), 3.45-3.60 (m, 5H, H-3, H-4, H-5, CH$_2$O), 3.66-3.72 (dd, J=12.0, 5.2 Hz, 2H, H-6a), 3.84-3.91 (m, 2H, H-2, H-6b), 4.19-4.21 (m, 1H, H-4'), 4.42-4.45 (m, 1H, H-3'), 4.56 (s, 2H, CH$_2$ triazole), 4.75-4.78 (m, 2H, H-5'), 5.22 (s, 2H, CH$_2$—N triazole), 5.58 (d, J=9.2 Hz, 1H, H-1), 6.24 (dd, J=6.0 Hz, 1H, H-1'), 7.31 (s, 1H, H-6 thymine), 8.00 (s, 1H, H triazole), 8.11 (s, 1H, H triazole).

$^{13}$C NMR (75 MHz, in MeOD) δ 11.80 (CH$_3$ thymine), 25.56, 25.80, 29.23, 29.26, 32.27 (CH$_2$ and CH$_2$CH$_2$O), 35.62 (CH$_2$N triazole), 38.21 (C-2'), 51.21 (C-5'), 60.92 (C-6), 61.60 (CH$_2$O), 63.14 (OCH$_2$ triazole), 70.33 (CH$_2$O), 69.41, 76.93, 79.67 (C-3 or C-4 or C-5), 71.00 (C-3'), 72.50 (C-2), 84.27 (C-4'), 86.53 (C-1'), 88.15 (C-1), 109.82 (C-5 thymine), 123.03, 124.82 (CH triazole), 135.47 (C-6 thymine), 143.12, 144.72 (C quat. triazole), 150.59, 163.37 (C=O thymine).

HRMS: (M+Na) 773.3795 (calculated 773.3804)

Example 2

1,12-bis-dodecanyl-5'-[(4-oxymethyl)-1H-1,2,3-triazole-1-yl)]-N-3-[1-((β-D-glucopyranoside)-1H-1,2,3-triazole-4-yl)methyl]-5'-deoxy thymidine (6)

To a solution of 4 obtained in preparation 4 (200 mg, 0.225 mmol) and 1-azido-β-D-glucopyranose (111 mg, 0.540 mmol) in 12 mL of THF/H$_2$O (1:1) was added copper sulfate (14 mg, 0.09 mmol) followed by sodium ascorbate (53 mg, 0.27 mmol). The mixture was irradiated under stirring in a microwave reactor (open vessel equipped with a reflux condenser) at 200 W and 75° C. for 5 min. The crude resulting mixture was concentrated under reduced pressure and purified by column chromatography on silica gel eluting with DCM/MeOH (8:2 to 7:3) to give 5 then 6. Yields: 5, 16 mg (9.5%); 6, 177 mg (58%).

$^1$H NMR (300 MHz, in MeOD) δ 1.28-1.35 (s, 16H, CH$_2$), 1.52-1.61 (m, 4H, CH$_2$CH$_2$O), 1.92 (s, 6H, CH$_3$ thymine), 2.27-2.31 (dd, J=6.0 Hz, 4H, H-2'), 3.48-3.60 (m, 10H, H-3, H-4, H-5, CH$_2$O), 3.67-3.73 (dd, J=12.0, 5.2 Hz, 2H, H-6a), 3.85-3.93 (m, 4H, H-2, H-6b), 4.17-4.22 (m, 2H, H-4'), 4.41-4.46 (m, 2H, H-3'), 4.56 (s, 4H, triazole CH$_2$O), 4.74-4.77 (m, 4H, H-5'), 5.21 (s, 4H, triazole CH$_2$N), 5.59 (d, J=9.2 Hz, 2H, H-1), 6.23 (dd, J=6.0 Hz, 2H, H-1'), 7.28 (s, 2H, H-6 thymine), 7.99 (s, 2H, H triazole), 8.13 (s, 2H, H triazole).

$^{13}$C NMR (75 MHz, in MeOD) δ 11.80 (CH$_3$ thymine), 25.76 (CH$_2$), 29.23 (CH$_2$CH$_2$O), 35.67 (CH$_2$N triazole), 38.21 (C-2'), 48.45 (C-5'), 60.95 (C-6), 63.16 (OCH$_2$ triazole), 69.42, 76.98, 79.69 (C-3, C-4, C-5), 70.32 (CH$_2$O), 70.98 (C-3'), 72.51 (C-2), 84.23 (C-4'), 86.63 (C-1'), 88.17 (C-1), 122.91, 124.79 (CH triazole), 135.44 (C-6 thymine).

HRMS: (M+Na) 1321.5802 (calculated 1321.5783)

Example 3

5'-[4-((β-D-Glucopyranosyloxy)dodecanyloxy)methyl)-1H-1,2,3-triazol-1-yl]-5'-deoxy-N-3-[1-((β-D-glucopyranoside)-1H-1,2,3-triazol-4-yl)methyl] thymidine (11)

To a degassed solution of compound 10 obtained in Preparation 7 (0.87 g, 1.49 mmol) in 24 mL THF/H$_2$O (6:4) was added 1-azido-β-D-glucopyranose (0.62 g, 3.00 mmol), copper sulfate (120.00 mg, 0.60 mmol) and sodium ascorbate (47.80 mg, 0.30 mmol). The mixture was stirred at 60° C. for 3 hours. After removal of the solvents in vacuo, the resulting green solid was dissolved in methanol and filtered through celite, the resulting solution was concentrated under reduced pressure and applied to a column of silica gel. The product was eluted with DCM/MeOH (8:2). Yield: 0.81 g (54%).

$^1$H NMR (300 MHz, in MeOD) δ 1.30-1.33 (m, 16H, CH$_2$), 1.50-1.62 (m, 4H, chain-CH$_2$CH$_2$O), 1.93 (d, J=1.0 Hz, 3H, CH$_3$ thymine), 2.26-2.47 (m, 1H, H-2'), 3.49-3.60 (m, 10H, 2 chain-CH$_2$O, H-3A, H-3B, H-4A, H-4B, H-5A, H-5B), 3.67-3.76 (2 dd, 2H, J=11.6, 5.2 Hz, H-6A,a and H-6B,a), 3.85-3.97 (m, 4H, H-6A,b, H-6B,a and H-2A, H-2B), 4.33-4.37 (m, 2H, H-3' and H-4'), 4.56 (s, 2H, triazole-CH$_2$O), 4.68-4.70 (d, J=4.7 Hz, 2H, triazole-CH$_2$O), 4.74-4.76 (m, 2H, H-5'), 5.22 (s, 2H, triazole-CH$_2$N), 5.58 (d, J=9.2 Hz, 1H, H-1A or H-1B), 5.65 (d, J=9.2 Hz, 1H, H-1B or H-1A), 6.19 (t, J=7.0 Hz, H-1'), 7.30 (d, 1H, H-6 thymine), 7.98, 8.13 and 8.25 (3 s, 1H, CH triazole).

$^{13}$C NMR (75 MHz, in MeOD) δ 11.75 (CH$_3$ thymine), 25.55, 25.80, 29.18, 29.22, 29.26, 29.33 (CH$_2$ and CH$_2$CH$_2$O), 32.26 (CH$_2$CH$_2$O), 32.50 (triazole-CH$_2$-thymine), 51.07 (C-5'), 60.94 (C-6A, C-6B), 61.58 (chain-CH$_2$O), 61.93 and 63.11 (triazole-CH$_2$O), 69.40, 69.44 (C-3, C-4 or C-5 A and B), 70.36 (chain-CH$_2$O), 72.49, 72.61 (C-2A, C-2B), 76.98, 77.01 (C-3, C-4 or C-5 A and B), 78.49, 82.12 (C-3', C-4'), 79.69, 79.74 (C-3, C-4 or C-5 A and B), 87.04 (C-1'), 88.17, 88.25 (C-1A, C-1B), 122.93, 123.18, 124.79 (CH triazole), 135.53 (C-6 thymine).

HRMS: (M+Na) 1016.4648 (calculated 1016.4859).

Example 4

1,12-bis-dodecanyl-5'-[4-(oxymethyl)-1H-1,2,3-triazol-1-yl]-5'-deoxy-3'-O-1-((β-D-glucopyranoside)-1-H-1,2,3-triazol-4-yl)methyl thymidine

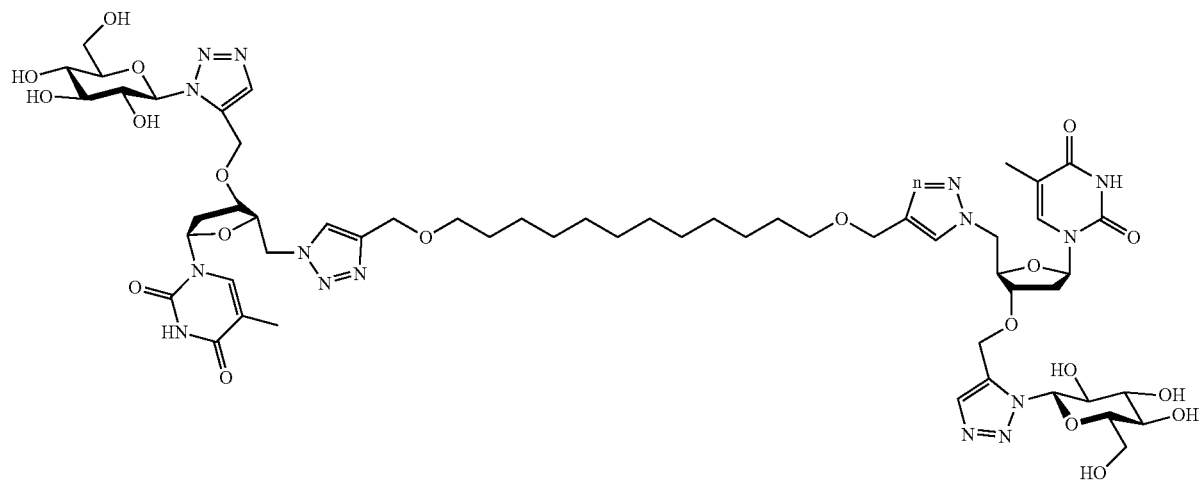

To a degassed solution of 7 obtained in preparation 1 (139.0 mg, 0.5 mmol) in 30 mL THF/H₂O (2:1) was added 5'-azido-5'-deoxy-3'-O-1-((β-D-glucopyranoside tetraacetate)-1H-1,2,3-triazol-4-yl)methyl thymidine [L. Latxague, A. Patwa, E. Amigues, P. Barthélémy, *Molecules* 18 (2013) 12241-63], copper sulfate (15.9 mg, 0.1 mmol) and sodium ascorbate (39.6 mg, 0.2 mmol). The mixture was stirred at 65° C. for 6 hours then overnight at rt. After removal of the solvents in vacuo, the remaining crude material was applied to a column of silica gel. The product was eluted with DCM/MeOH (95:5) then subjected to a Zemplen deacetylation. Yield: 301 mg (46%).

$^1$H NMR (300 MHz, in MeOD @ 323K) δ 1.30 (s, 16H, CH₂), 1.55-1.63 (m, 4H, CH₂CH₂O), 1.91 (s, 6H, CH₃ thymine), 2.22-2.31 (m, 2H, H-2'a), 2.39-2.47 (m, 2H, H-2'b), 3.39 (t, J=6.5 Hz, 4H, CH₂CH₂O), 3.54-3.66 (m, 6H, H-3, 4, 5), 3.74-3.81 (m, 2H, H-6a), 3.91-4.00 (m, 4H, H-2, 6b), 4.34-4.39 (m, 4H, H-3', 4'), 4.60 (s, 4H, OCH₂ triazole), 4.71-4.76 (m, 8H, H-5' and OCH₂ triazole), 5.66 (d, J=9.2 Hz, 2H, H-1), 6.18 (dd, J=6.7 Hz, 2H, H-1'), 7.22 (s, 2H, H-6 thymine), 7.96 (s, 2H, H triazole), 8.21 (s, 2H, H triazole).

$^{13}$C NMR (75 MHz, in MeOD @ 323K) δ 9.75 (CH₃ thymine), 24.49 (CH₂), 27.76, 27,89, 27,97 (CH₂ and CH₂CH₂O), 34.39 (C-2'), 49.87 (C-5'), 59.91 (C-6), 60.97 and 62.07 (CH₂ triazole), 68.47, 75.95, 78.55 (C, 3, 4, 5), 69.20 (CH₂CH₂O), 71.49 (C-2), 77.42, 80.77 (C-3', 4'), 84.60 (C-1'), 87.08 (C-1), 109.44 (C-5 thymine), 121.88, 123.43 (CH triazole), 135.32 (C-6 thymine), 142.91, 143.87 (C-4 triazole), 149.51, 163.46 (C=O thymine).

Example 5

1,10-bis-2,2,3,3,4,4,5,5,6,6,7,7,8,8,9,9-hexafluorodecanyl-5'-[4-(oxymethyl)-1H-1,2,3-triazol-1-yl]-N-3-[1-((β-D-glucopyranoside)-1H-1,2,3-triazol-4-yl)methyl]-5'-deoxythymidine

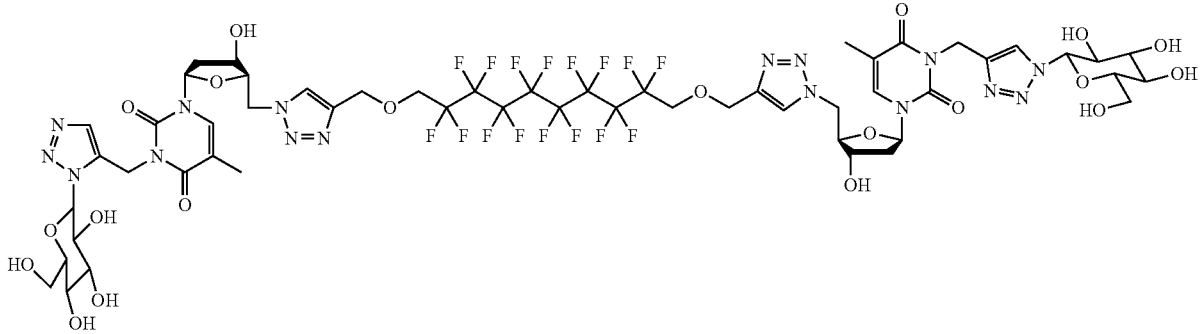

Figure 1:
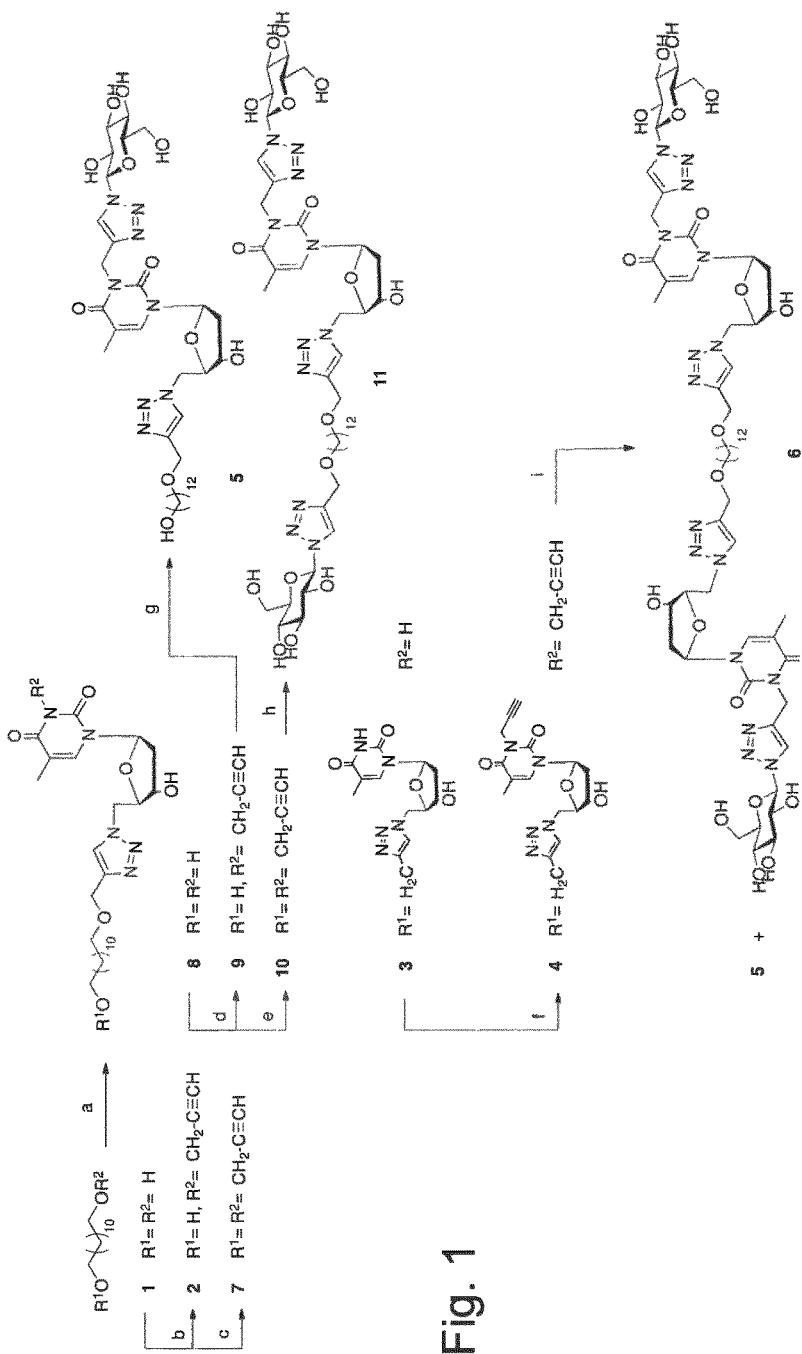
FIG. 1 shows the synthetic scheme used in the Preparations and Examples for compounds of formula (I) in which X is oxygen.
Figure 2:
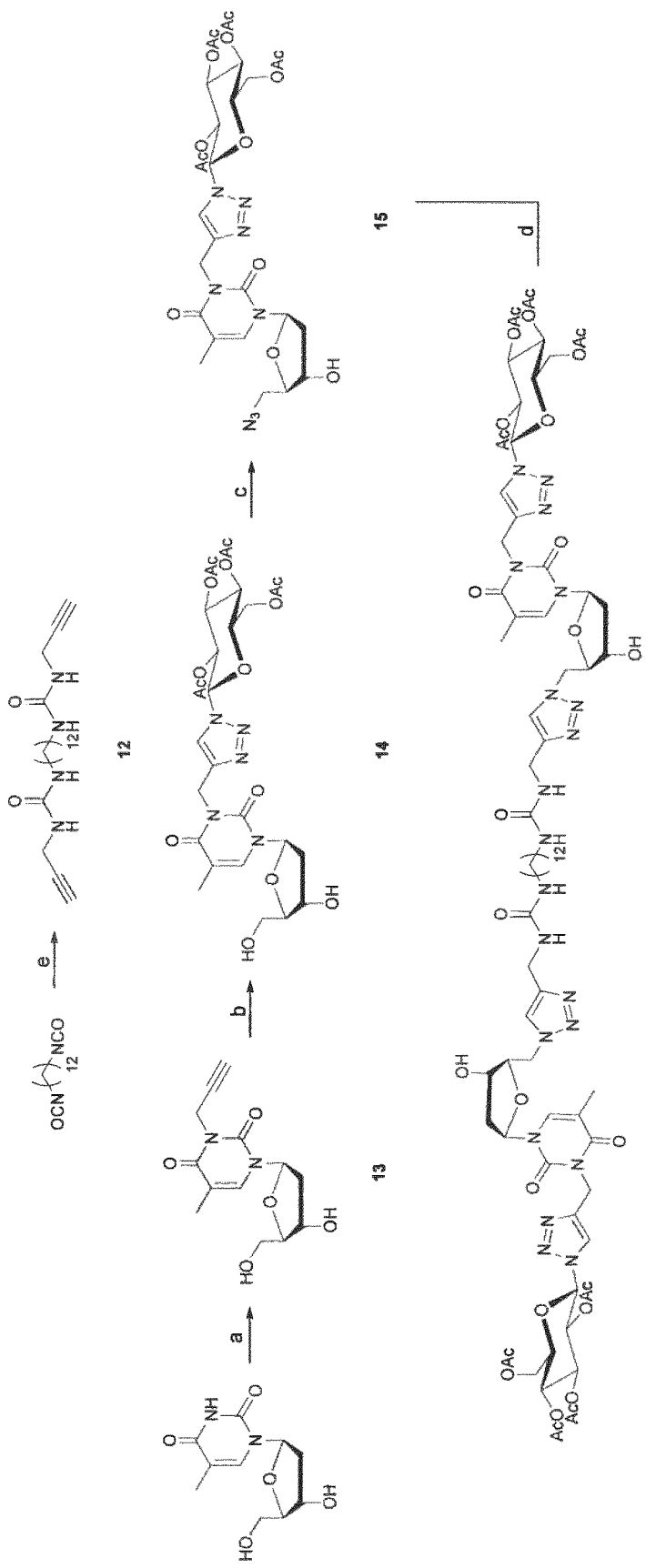
FIG. 2 shows the synthetic scheme used in the Preparations and Examples for compounds of formula (I) in which X is —NH—C(O)—NH—.
Figure 3:
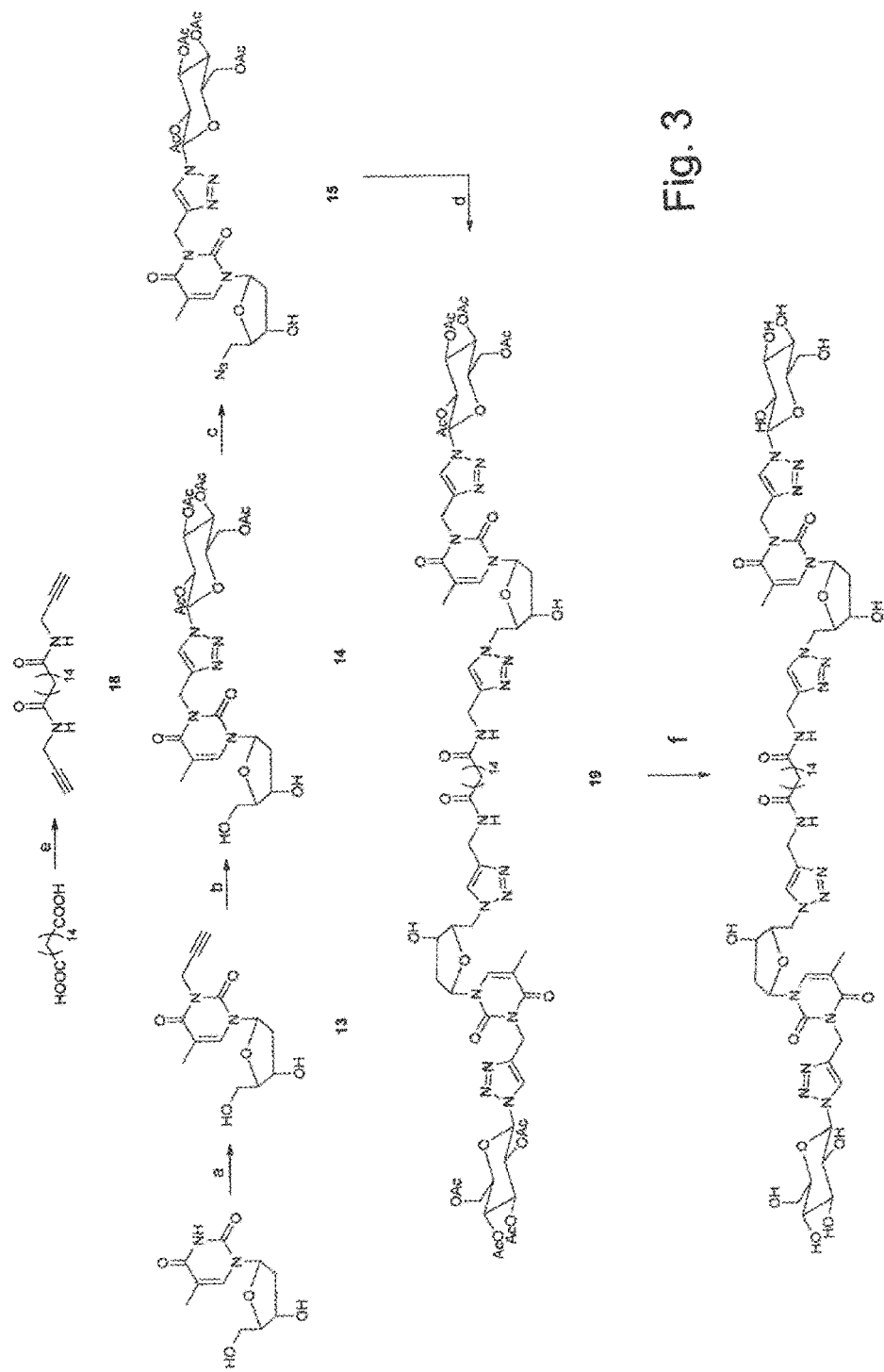
FIG. 3 shows the synthetic scheme used in the Preparations and Examples for compounds of formula (I) in which X is —NH—C(O)—.

To a degassed solution of 1,10-bis-2,2,3,3,4,4,5,5,6,6,7,7,8,8,9,9-hexafluorodecanyl-5'-[4-(oxymethyl)-1H-1,2,3-triazol-1-yl]-N-3-propargyl-5'-deoxythymidine obtained from commercial 2,2,3,3,4,4,5,5,6,6,7,7,8,8,9,9-hexadecafluoro-1,10-decanediol subjected to a similar set of reactions as shown in FIG. 1, namely propargylation/azidothymidine coupling/nucleobase propargylation) (782.00 mg, 0.68 mmol) in 15 mL THF/H₂O (2:1) was added 1-azido-1-deoxyglucopyranose, copper sulfate (26.90 mg, 0.14 mmol) and sodium ascorbate (43.40 mg, 0.27 mmol). The mixture was stirred at 60° C. overnight. After removal of the solvents in vacuo, the remaining crude material was washed with water and the filtrate was concentrated under reduced pressure. The oily residue was applied to a column of silica gel. The product was eluted with DCM/MeOH (8:2 then 7:3). Yield: 514.00 mg (48%).

$^1$H NMR (300 MHz, in MeOD) d 1.91 (d, J=1.1 Hz, 6H, CH$_3$ thymine), 2.28-2.32 (t, J=6.2 Hz, 4H, H-2'), 3.47-3.58 (m, 6H, H-2,3,5), 3.66-3.71 (dd, J=5.1, 12.1 Hz, 2H, H-6a), 3.83-3.90 (m, 4H, H-4, 6b), 4.09-4.18 (t, J=14.1 Hz, 4H, CH$_2$CF$_2$), 4.17-4.22 (m, 2H, H-4'), 4.40-4.45 (dd, J=5.2 Hz, 2H, H-3'), 4.74-4.79 (m, 8H, H-5' and OCH$_2$ triazole), 5.20 (s, 4H, OCH$_2$ triazole), 6.56 (d, J=9.2 Hz, 2H, H-1), 6.20 (dd, J=6.7 Hz, 2H, H-1'), 7.29 (d, 2H, H-6 thymine), 8.05 (s, 2H, H triazole), 8.10 (s, 2H, H-triazole).

$^{13}$C NMR (75 MHz, in MeOD) d 10.14 (CH$_3$ thymine), 34.15 (OCH$_2$ triazole), 36.72 (C-2'), 49.76 (C-5'), 59.47 (C-6), 63.11 (OCH$_2$ triazole), 64.97 (t, $^2J_{C-F}$=26.0 Hz, CH$_2$CF$_2$), 67.98, 75.54, 78.22 (C2, 3 or 5), 69.60 (C-3'), 71.05 (C-4), 82.80 (C-4'), 85.44 (C-1'), 86.72 (C-1), 108.26 (C-5 thymine), 121.36, 123.75 (CH triazole), 134.00 (C-6 thymine), 141.91 (C-4 triazole), 149.05 and 161.87 (C=O thymine).

Example 6

1,12-bis-dodecanyl-5'-[(4-methylurea)-1H-1,2,3-triazol-1-yl]-N-3-[1-((2,3,4,6-tetra-O-acetyl-β-D-glucopyranoside)-1H-1,2,3-triazole-4-yl)methyl]-5'-deoxythymidine (16)

To a solution of 15 obtained in Preparation 11 (1 g, 1.47 mmol) in 36 mL of tert-butanol/H$_2$O (1:1) was added compound 12 obtained in Preparation 8 (243 mg, 0.67 mmol), copper sulfate (33 mg, 0.13 mmol) and sodium ascorbate (53 mg, 0.27 mmol). The mixture was stirred at 75° C. for 20 hours. The solvent was removed under reduced pressure and the residual solid was dissolved in DCM (150 mL) and then washed with water (3×50 mL). The organic extract was dried (Na$_2$SO$_4$) and concentrated under reduced pressure. The crude product was purified by chromatography on silica gel eluting with ethyl acetate/MeOH (10:0 to 90:10) and obtained as a white solid. Yield: 0.90 g (78%).

$^1$H NMR (300 MHz, in DMSO-d$_6$) δ 1.23-1.32 (m, 20H, chain CH$_2$), 1.76-2.00 (m, 15H), 2.17 (m, 2H), 2.95 (q, 4H), 4.08 (m, 6H), 4.20-4.36 (m, 8H), 4.57-4.73 (m, 4H), 4.97-5.11 (q, 4H), 5.16 (t, 2H), 5.54 (m, 2H), 5.66 (t, 2H), 6.21 (t, 2H), 6.31 (d, 2H), 7.50 (s, 2H), 7.85 (s, 2H), 8.26 (s, 2H).

$^{13}$C NMR (75 MHz, in DMSO-d$_6$) δ 13.12, 20.32-20.96, 35.41, 36.36, 38.54, 51.53, 62.27, 67.97, 70.38, 71.18, 72.68, 72.85, 73.73, 84.20, 84.74, 85.72, 109.18, 123.07, 135.55, 143.81, 150.61, 158.32, 162.69, 168.68, 169.82, 170.03, 170.51.

Example 7

1,12-bis-dodecanyl-5'-[(4-methylurea)-1H-1,2,3-triazol-1-yl]-N-3-[1-((β-D-glucopyranoside)-1H-1,2,3-triazole-4-yl)methyl]-5'-deoxy thymidine (17)

A solution of sodium methoxide (1 M in methanol, 0.2 mL) was added dropwise to a solution of compound 16 prepared in example 6 (0.49 g, 0.28 mmol) in 20 mL of methanol anhydrous. After heating for 1 h minutes at 60° C., amberlite IRC-50 was added to convert from Na$^+$ to H$^+$ ions. After 20 minutes at the same temperature, the resin was removed by filtration and washed with methanol. The filtrate was concentrated and the product was purified by column chromatography on silica gel eluting with MeOH:CH$_2$Cl$_2$ (30:70 to 50:50) to afford as a white solid (Yield: 79%, 0.31 g).

$^1$H NMR (300 MHz, in MeOD) δ 1.26-1.41 (m, 20H), 1.89 (s, 3H), 2.24-2.29 (m, 4H), 3.03-3.07 (t, 4H), 3.40-3.54 (m, 6H), 3.62-3.68 (dd, 2H), 3.81-3.86 (m, 4H), 4.06-4.16 (m, 2H), (4.12 (s, 4H), 4.32-4.39 (m, 2H), 4.60-4.74 (m, 4H), 4.02 (s, 6, 160.89, 164.79.

Example 8

1,14-bis-tetradecanyl-5'-[(4-methylamide)-1H-1,2,3-triazol-1-yl]-N-3-[1-((2,3,4,6-tetra-O-acetyl-β-D-glucopyranoside)-1H-1,2,3-triazole-4-yl)methyl]-5'-deoxy thymidine (19)

To a solution of compound 18 (0.24 g, 0.67 mmol) and compound 15 (1 g, 1.47 mmol, 2.2 eq.) in 36 mL of tert-Butanol/H2O (1:1) was added sodium ascorbate (53 mg, 0.27 mmol, 0.4 eq.) followed by copper sulfate pentahydrate (33 mg, 0.13 mmol, 0.2 eq.). The mixture was stirred at 75° C. for 24 hours.

After cooling to room temperature, the solvents were removed under reduced pressure. The resulting solid was dissolved in DCM and the solution was washed with water. The organic layer was dried over Na$_2$SO$_4$, filtered and concentrated. The product was purified by column chromatography on silica gel eluting with ethyl acetate/MeOH (100:0 to 80:20) to afford as a white solid (Yield: 76%, 0.87 g).

$^1$H NMR (300 MHz, DMSO-d$_6$) δ 1.21 (s, 20H), 1.43-1.49 (m, 4H), 1.76-2.03 (m, 24H), 1.87 (s, 6H), 2.04-2.09 (t, J=7.5 Hz, 4H), 2.12-2.23 (m, 4H), 4.03-4.14 (m, 6H), 4.26-4.37 (m, 8H), 4.58-4.73 (m, 4H), 4.97-5.11 (m, 4H), 5.14-5.20 (t, J=9.8 Hz, 2H), 5.49-5.54 (t, J=9.6 Hz, 2H), 5.49-5.54 (d, 2H), 5.63-5.69 (t, J=9.4 Hz, 2H), 6.20-6.24 (t, J=6.6 Hz, 2H), 6.28-6.32 (d, J=9.2 Hz, 2H), 7.49 (s, 2H), 7.90 (s, 2H), 8.25 (s, 2H), 8.25-8.29 (m, 2H).

$^{13}$C NMR (75 MHz, DMSO-d$_6$) δ 12.68, 20.33, 20.70, 20.84, 20.97, 25.65, 29.16, 29.26, 29.41, 29.53, 34.07, 35.21, 35.92, 38.12, 51.11, 61.83, 67.52, 70.00, 70.72, 72.22, 73.29, 83.74, 84.27, 85.24, 109.05, 122.62, 123.48, 135.11, 143.33, 145.14, 150.17, 162.23, 168.42, 169.36, 169.57, 170.04, 172.10.

Example 9

1,14-bis-tetradecanyl-5'-[(4-methylamide)-1H-1,2,3-triazol-1-yl]-N-3-[1-((β-D-glucopyranoside)-1H-1,2,3-triazole-4-yl)methyl]-5'-deoxy thymidine (20)

A solution of sodium methoxide (1 M in methanol, 0.2 mL) was added dropwise to a solution of compound 19 prepared in example 8 (0.64 g, 0.37 mmol) in 20 mL of methanol anhydrous. After heating for 30 minutes at 45° C., Amberlite IRC-50 was added to convert from Na$^+$ to H$^+$ ions. After 20 minutes at the same temperature, the resin was removed by filtration and washed with methanol. The filtrate was concentrated and the product was purified by column chromatography on silica gel eluting with MeOH:CH$_2$Cl$_2$ (30:70 to 50:50) to afford as a white solid (Yield: 84%, 0.46 g).

$^1$H NMR (300 MHz, MeOD) δ 1.22 (s, 20H), 1.48-1.57 (m, 4H), 1.87 (s, 6H), 2.11-2.16 (t, 4H), 2.22-2.27 (m, 4H), 3.41-3.51 (m, 6H), 3.64-3.70 (dd, 2H), 3.79-3.85 (m, 4H), 4.13-4.18 (m, 2H), 4.33-4.39 (m, 6H), 4.63-4.77 (m, 4H), 5.16 (s, 4H), 5.51-5.54 (d, 2H), 6.13-6.17 (t, 2H), 7.28 (s, 2H), 7.82 (s, 2H), 8.06 (s, 2H).

$^{13}$C NMR (75 MHz, MeOD) δ 13.15, 26.89, 30.25, 30.38, 30.56, 30.66, 30.69, 35.57, 36.92, 37.06, 39.59, 52.73, 62.37, 70.87, 72.56, 73.94, 78.42, 81.13, 85.82, 88.31, 89.61, 111.15, 124.29, 125.34, 137.07, 144.58, 146.39, 151.95, 164.77, 176.27.

Example 10: Gelation Test

The aqueous dispersions (Milli-Q water, 18 MΩ·cm$^{-1}$) containing 1.5 wt % of compounds 5 and 6 obtained in examples 1 and 2 were heated until dissolution (at 45° C.) and gradually allowed to cool to room temperature unless otherwise stated. The resulting solid aggregate mass was stable to inversion of the container when the test tube was turned upside down, which shows that the compounds 5 and 6 form gels.

Example 11: Rheology

Rheological measurements were carried out on a Malvern Kinexus Pro+ rheometer with steel plate-plate geometry (20 mm diameter). The lower plate is equipped with a Peltier temperature control system, and all samples were studied at 25±0.01° C. unless indicated otherwise. A solvent trap was used to ensure homogeneous temperature and to prevent water evaporation. A gap distance of 0.3 mm was maintained between the plates. The gels based on compounds 5 (example 1) and 6 (example 2) (obtained in example were heated at 55° C. and the liquid resulting was placed into the rheometer and subjected to sinusoidal oscillations. All the measurements were carried out within the linear viscoelastic regime (LVR). For this purpose the experimental conditions to achieve a linear viscoelastic regime were determined by performing an amplitude strain sweep from 0.01 to 10% at an angular frequency of 1 Hz (6.283 rad·s$^{-1}$).

Figure 4:
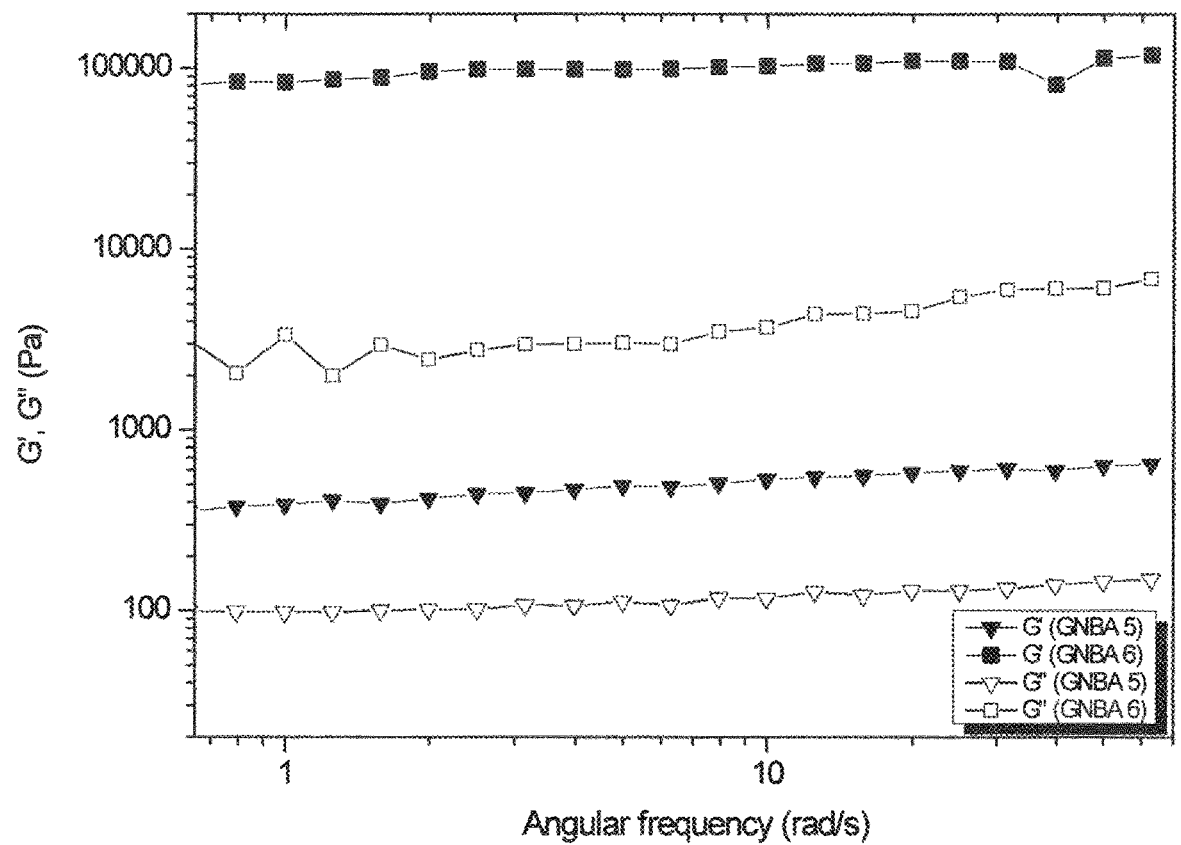
FIG. 4 shows the frequency sweep results for hydrogels obtained from compounds 5 and 6.

FIG. 4 shows the frequency sweep results for hydrogels obtained from compound 5 and 6 (at 23.10 mM) at a constant strain of 0.03%.

Figure 5:
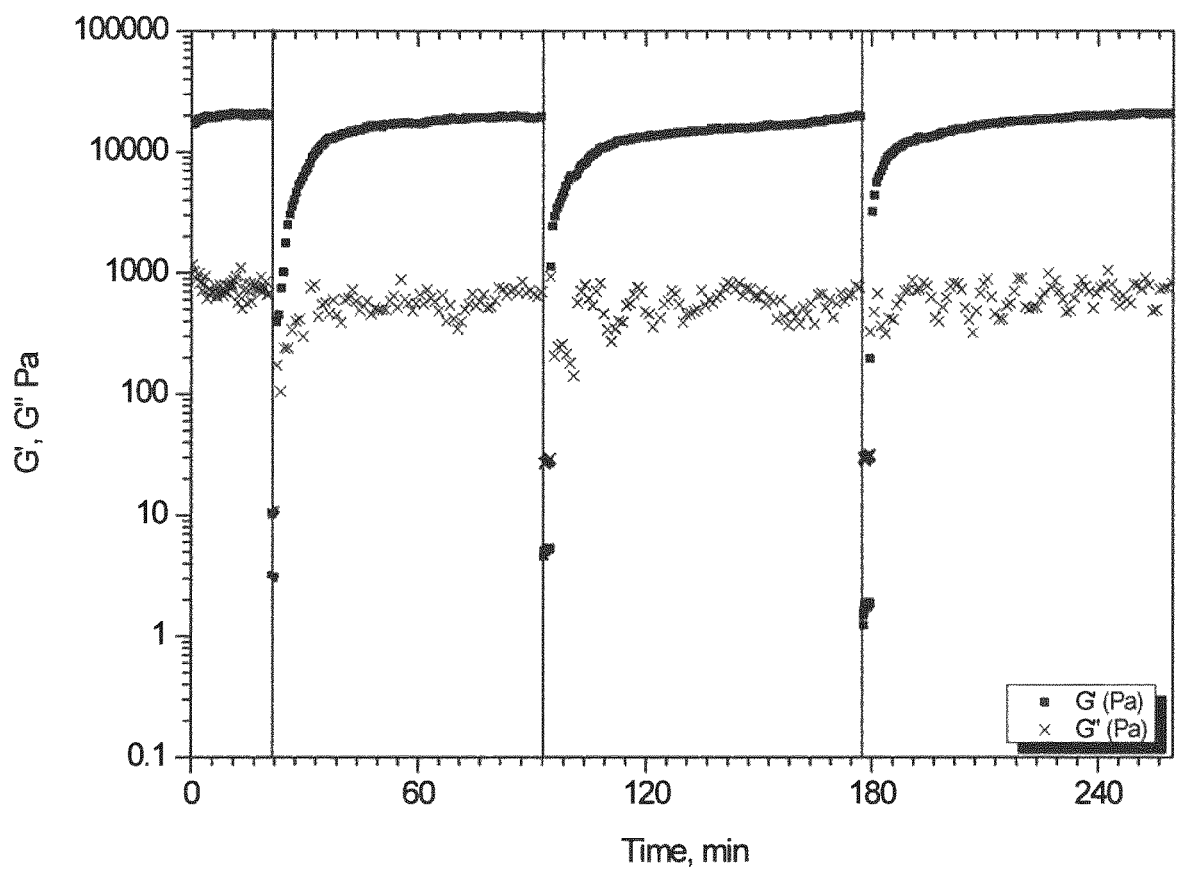
FIG. 5 shows the step-strain measurement of the hydrogel obtained from compound 6.

FIG. 5 shows the step-strain measurement of the hydrogel obtained from compound 6 at 1% (w/v) at a fixed angular frequency of 6.283 rad·s$^{-1}$. This experiment was repeated at least three times to verify its reproducibility.

These results show the thixotropic behaviour of the hydrogel according to the invention. The mechanical energy which is provided destabilizes the gel, which is able to auto-regenerate when the mechanical stress stops, without causing aging of the sample (several stress/restauration of G' and G" modulus were observed).

Sol-Gel Transition Temperature ($T_{gel}$)

The determination of gel-sol transition temperature can also be determined by rheology. The hydrogel (3% product 6 of example 2, w/v) was heated progressively from 25 to 60° C. (3° C./min). The oscillatory stress applied was set to 5 Pa at a constant frequency (1 Hz). The sol-gel transition point was taken as the temperature at which the gel became liquid. This melting temperature is reached at the intersection of the viscoelastic moduli (G' and G"). This value is of 46° C. which is compatible with the cell culture at the gel state (37° C.).

Example 12: Cytotoxicity and Cytocompatibility

The experiments were performed using compound 6 of example 2, namely the 1,12-bis-dodecanyl-5'-[(4-oxymethyl)-1H-1,2,3-triazole-1-yl)]-N-3-[1-((β-D-glucopyranoside)-1H-1,2,3-triazole-4-yl)methyl]-5'-deoxy thymidine.

a) Cell Culture—Isolation and Culture of hASCs

Mesenchymal stem cells were isolated from human adipose tissue. Human subcutaneous fat was obtained from healthy patients aged 20 to 80 years old who underwent hip surgery in Bordeaux Pellegrin CHU (Bordeaux, France). Fat mass was separated from other tissues, washed with sterilized PBS, finely cut and incubated with 0.1% (w/v) collagenase type I (Worthington, Lakewood, N.J., USA) at 37° C. with gentle agitation for 1 h 30. After filtration and centrifugation, the top liquid layer was removed and the remaining Stromal Vascular Fraction (SVF) was treated for 10 min with ELB (Erythrocyte Lysis Buffer; 155 mM NH$_4$Cl (Sigma-Aldrich, St. Louis, Mo., USA), 5.7 mM K$_2$HPO$_4$, 7.4 mM K$_2$HPO$_4$-3H$_2$O, 0.1 mm EDTA (all Sigma-Aldrich)), and then centrifuged. The pellet was resuspended in DMEM F12 medium (Invitrogen/Life Technologies, Sergy Pontoise, France) supplemented with 10% (v/v) Foetal Bovine Serum (FBS) (Lonza, Basel, Switzerland) and sequentially filtered through 100, 70 and 40 μm cell strainer (BD Falcon, Franklin Lakes, N.J., USA). Cells were plated and cultivated at 37° C. in 5% CO$_2$. Culture medium was replaced every two days.

b) Cell Culture—D1-ORL-UVA

D1-ORL-UVA (ATCC® CRL-12424) were cultured in DMEM (Invitrogen/Life Technologies) containing 10% FBS, and 1% Penicillin-Streptomycin (Invitrogen/Life Technologies). Culture medium was replaced every two days.

c) Preparation of 3D Scaffold with hASCs or D1 Seeding

For all in vitro assays, the hydrogel obtained from compound 6 was prepared at a concentration of 3% (w/v). The compound 6 powder was solubilized in PBS 1× under agitation (900 rpm) at 25° C. during 45 minutes. Then, when the gel was formed, it was left at room temperature, without agitation, during 3 to 4 hours. To allow cell seeding, the gel was heated during 30 minutes at 55° C. Once the liquid solution was obtained, it was rapidly cooled down to 37° C. and thoroughly mixed with 10 μL cell suspension at a concentration of 1 million cells per mL of gel. Finally, the cellularized hydrogel was maintained under agitation (600 rpm), at 25° C. during 45 minutes. After this period, medium was been added (250 μL/tube) and tubes were incubated at controlled atmosphere (5% CO$_2$, 37° C.)

d) Evaluation of Compound 6 Cytotoxicity and of BOLA Gel Cytocompatibility

The cytotoxicity of compound 6 was evaluated by the measurement of the cell metabolic activity (MTT assay). This tests uses tetrazolium bromide MTT (3-(4,5-dimethylthiazol-2-yl)-2,5-diphenyl tetrazolium bromide) which is reduced into formazan by the mitochondrial enzyme succinate deshydrogenase of living cells. This reduction results in a change of colour from yellow to violet-blue. The colour intensity is proportional to the amount of living cells.

Cells (hASCs or D1) were seeded in a 96 wells plate (Nunc) at a density of 10 000 cells/cm$^2$. Product 6 was solubilized at concentrations from 5 μM to 5 mM in culture media.

MTT assay was performed after 72 h of incubation. As a positive control, the culture medium without GNBA was used. As a negative control, Triton X100 was added in the culture medium. Results were expressed as a percentage of the metabolic activity of the positive control. Absorbance was measured at a wavelength of 570 nm with background subtraction at 630 nm.

The cytotoxicity of compound 6 was determined by MTT test to measure the metabolic activity of human mesenchymal stem cells (ASCs) 48 hours after incubation with increasing concentrations of compound 6. Results are shown as percentage of positive control consisting in BOLA-free cell culture medium. **: p<0.01 (Mann-Whitney U-Test).

Figure 6:
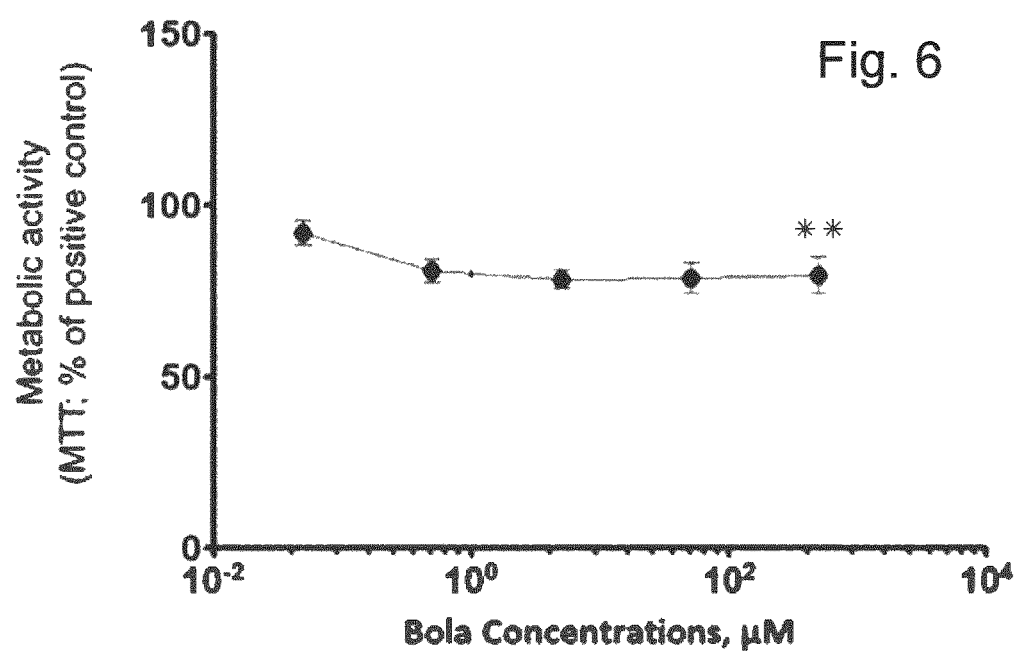
FIG. 6 shows the determination of the cytotoxicity of compound 6 by MTT test on human mesenchymal stem cells.

The results, represented on FIG. 6, show that compound 6 is non toxic at concentrations up to approximately 1 mM.

Figure 7A:
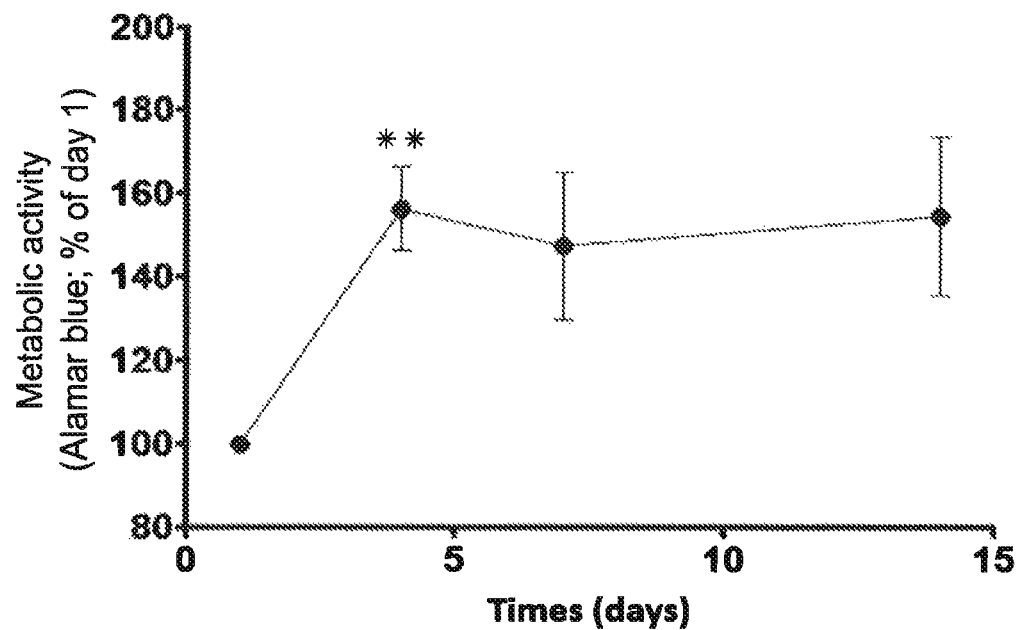
FIG. 7A shows the cytocompatibility of compound 6 by monitoring alamar blue metabolism in rat osteoblastic cells grown in compound 6-based gels.

Cell viability was also evaluated by using the Alamar Blue metabolic activity assay. Resazurin sodium salt solution (Sigma-Aldrich), suspended at a concentration of 0.1 mg/ml in PBS 1x), was diluted at 1/10 (v/v) in the culture media. The solution was added to each well (250 μL) and incubated during 3 h at 37° C. After this time, the fluorescence was measured at wavelengths excitation 530 nm and emission 590 nm. Triplicate samples were analyzed for each experiment. The results are shown on FIG. 7A.

Cytocompatibility was determined by monitoring alamar blue metabolism in rat osteoblastic cells (A) or human ASCs (B) grown in compound 6-based gels. Results are shown as percentage of the value obtained at day 1. *: p<0.05; **: p<0.01 (Mann-Whitney U-Test).

Figure 7B:
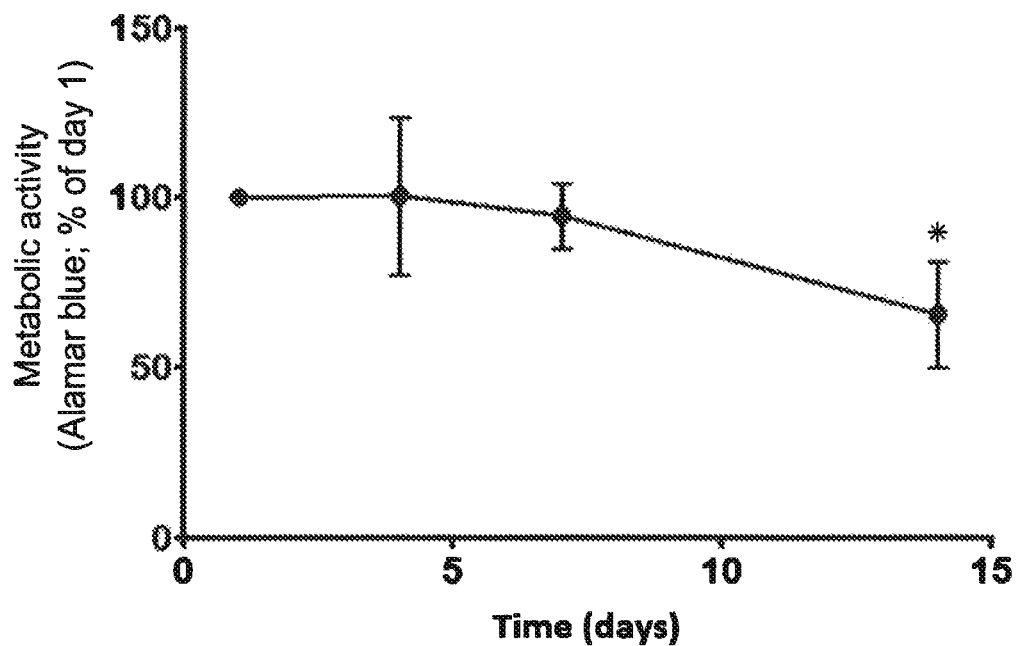
FIG. 7B shows the cytocompatibility of compound 6 by monitoring alamar blue metabolism in human stem cells ASCs grown in compound 6-based gels.

The results are shown on FIG. 7B.

Viability was assessed after 1, 4 and 7 days by using Live/Dead staining with calcein-AM and ethidium homodimer (Molecular Probes, Invitrogen, USA). Cells seeded within gels were incubated for 1 h at 37° C. in Hank's medium supplemented with 1.25 μL calcein-AM and 5 μL EthD-1. Samples were observed with a Confocal microscope (Leica TCS SPE).

Live/dead staining at 2 weeks showed a vast majority of green (living) cells.

The results show that compound 6 is not cytotoxic and has a god cytocompatibility when used as cell culture medium.

Example 13 (Comparative Example) Cytotoxycity of Compound GNL of G. Godeau et al., Chem. Comm., 2009, 34, 5127-5130

The toxicity of the compound GNL disclosed in G. Godeau et al., on page 5127, right column, was evaluated in human hepatic carcinoma cells HuH-7 by MTT assay, in order to measure cellular mortality.

Huh-7 cells were grown in DMEM medium supplemented with 10% foetal calf serum, 2 mM L-glutamine and 1% non-essential amino acids, at 37° C. in a 5% CO2 atmosphere. All culture reagents were purchased from Invitrogen. 2000 Huh-7 cells per well were seeded into a 96-well plate and incubated the following day with increasing concentrations of compound GNLin complete growth medium. After 5 days in the presence of the compounds, the living cells were quantified by the colorimetric CellTiter Aqueous One Solution Cell Proliferation Assay (Promega), as recommended.

The viability results are shown on FIG. 8.

The results show that the GNL compound does not have a significant toxicity for concentrations which are equal to or lower than 100 μM. For higher concentration, toxicity quickly becomes important and 100% of the cells die at a concentration of 200 μM.

The invention claimed is:
1. A compound of formula (IV)

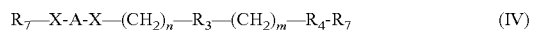

$$R_7-X-A-X-(CH_2)_n-R_3-(CH_2)_m-R_4-R_7 \qquad (IV)$$

in which
X is —NH—C(O)—NH—;
A is a $C_4$-$C_{30}$ hydrocarbon chain, linear or branched, saturated or unsaturated, which is unsubstituted or substituted by one or more $C_1$-$C_{12}$ linear or branched alkyl groups, or A represents a $C_4$-$C_{30}$ hydrocarbon chain, linear or branched, saturated or unsaturated, which is partially or completely halogenated;
$R_3$ represents a heteroaryl group comprising 1 to 4 oxygen or nitrogen atom(s);
$R_4$ represents a nucleosidyl group;
$R_7$ is the residue of an alkylating agent of formula R—$(CH_2)$q-C≡CH where q is 1 or 2 and R is a halide, wherein $R_7$ is linked by a covalent bond with a nitrogen atom of the purine, pyrimidine or universal base moiety of $R_4$;
n and m, identical or different, are 0 to 10.
2. A compound of formula (V),

$$R_4-(CH_2)_p-R_5-R_6 \qquad (V)$$

in which
$R_4$ represents a nucleosidyl group;
$R_5$ represents a heteroaryl group comprising 1 to 4 heteroatom(s), which is linked to $R_4$ by a covalent bond to a nitrogen atom of the pyrimidine base or of the purine base of the nucleosidyl group $R_6$ represents a residue of a cyclic carbohydrate or a derivative of the said carbohydrate, optionally substituted;
p is 0 to 10,
which is selected from 5'-deoxy-N3-(1-(2,3,4,6-tetra-O-acetyl-β-D-glucopyranoside)-1H-1,2,3-triazol-4-yl) thymidine, and 5'-Azido-N3-(1-(2,3,4,6-tetra-O-acetyl-β-D-glucopyranoside)-1H-1,2,3-triazol-4-yl) thymidine.

* * * * *